US007037509B2

(12) United States Patent
Koelle et al.

(10) Patent No.: US 7,037,509 B2
(45) Date of Patent: May 2, 2006

(54) IMMUNOLOGICALLY SIGNIFICANT HERPES SIMPLEX VIRUS ANTIGENS AND METHODS FOR USING SAME

(75) Inventors: David M. Koelle, Seattle, WA (US); Nancy A. Hosken, Seattle, WA (US); Christine M. Posavad, Seattle, WA (US); Hongbo Chen, Shoreline, WA (US); Patrick McGowan, Seattle, WA (US)

(73) Assignees: University of Washington, Seattle, WA (US); Fred Hutchinson Cancer Research Center, Seattle, WA (US); Corixa Corporation, Seattle, WA (US)

( * ) Notice: Subject to any disclaimer, the term of this patent is extended or adjusted under 35 U.S.C. 154(b) by 0 days.

(21) Appl. No.: 10/882,074

(22) Filed: Jun. 30, 2004

(65) Prior Publication Data

US 2004/0241182 A1    Dec. 2, 2004

Related U.S. Application Data

(62) Division of application No. 10/210,428, filed on Jul. 31, 2002, now Pat. No. 6,814,969.

(60) Provisional application No. 60/309,428, filed on Aug. 1, 2001, provisional application No. 60/308,923, filed on Jul. 31, 2001.

(51) Int. Cl.
*A61K 39/12* (2006.01)
(52) U.S. Cl. ............................... 424/229.1; 424/204.1; 435/6; 536/23.72
(58) Field of Classification Search ............. 424/229.1, 424/204.1; 435/6; 536/23.72; 530/300
See application file for complete search history.

(56) References Cited

U.S. PATENT DOCUMENTS

| 4,859,587 | A |   | 8/1989  | Roizman |
| 5,632,992 | A |   | 5/1997  | Nesburn et al. |
| 5,714,152 | A |   | 2/1998  | Burke et al. |
| 6,017,735 | A | * | 1/2000  | O'Hare et al. ............. 435/69.7 |
| 6,635,258 | B1|   | 10/2003 | Burke ..................... 424/231.1 |

FOREIGN PATENT DOCUMENTS

| WO | WO 92/02251   |   | 2/1992 |
| WO | WO 97/05265   |   | 2/1997 |
| WO | WO 98/04708   | * | 2/1998 |
| WO | WO 98/20016   |   | 5/1998 |
| WO | WO 00/08051   |   | 2/2000 |
| WO | WO 01/23414 A2|   | 5/2001 |

OTHER PUBLICATIONS

E. De Plaen et al., "Cloning of Genes Coding for Antigens Recognized by Cytolytic T Lymphocytes," Immunology Methods Manual, 1997, 692-718.
A. Dolan et al., "The Genome Sequence of Herpes Simplex Virus Type 2," Journal of Virology, 1998, 72(3):2010-2021.
G. Elliott and P. O'Hare, "Intercellular Trafficking and Protein Delivery by a Herpesvirus Structural Protein," Cell, 1997, 88:223-233.
D.M. Koelle et al., "Antigenic Specificities of Human $CD^+$ T-Cell Clones Recovered from Recurrent Genital Herpes Simples Virus Type 2 Lesions," Journal of Virology, 1994, 68(5):2803-2810.
D.M. Koelle et al., "CD8 CTL from Genital Herpes Simplex Lesions Recognition of Viral Tegument and Immediate Early Proteins and Lysis of Infected Cutaneous Cells," The Journal of Immunology, vol. 166(6): 4049-4058, Mar. 2001.
D.M. Koelle et al., "Clearance of HSV-2 from Recurrent Genital Lesions Correlates with Infiltration of HSV-Specific Cytotoxic T Lymphoctyes," The Journal of Clinical Investigation, 1998, 101(7):1500-1508.
D.M. Koelle et al., "Direct Recovery of Herpes Simplex Virus (HSV)-Specific T Lymphocyte Clones from Recurrent Genital HSV-2 Lesions," The Journal of Infectious Diseases, 1994, 169:956-61.
D.M. Koelle et al., "Preferrential Presentation of Herpes Simplex Virus T-Cell Antigen by HLA DQA1*0501/DQB1*0201 in Comparison to HLA DQA1*0201/DQB1*0201," Human Immunology, 1997, 53(2):195-205.
D.M. Koelle et al., "Recognition of Herpes Simplex Virus Type 2 Tegument Proteins by CD4 T Cells . . . " Journal of Virology, 1998, 72(9): 7476-7483.
D.M. Koelle, "The Roles of T Lymphocytes in Host Responses to Herpes Simplex Virus," Herpes, 1995, 2:83-88.
W.W. Kwok et al., "Peptide Binding Affinity and pH Variation Establish Functional Thresholds for Activation of HLA-DQ-Restricted T Cell Recognition," Human Immunology, 1999, 60(7);619-626.
Paoletti, "Applications of Pox Virus Vectors to Vaccination: An Update," Proceedings of the National Academy of Science USA, Oct. 1996, 93:11349-11353.

(Continued)

*Primary Examiner*—Ali R. Salimi
(74) *Attorney, Agent, or Firm*—Gates & Cooper LLP

(57) ABSTRACT

The invention provides HSV antigens that are useful for the prevention and treatment of HSV infection. Disclosed herein are epitopes confirmed to be recognized by T-cells derived from herpetic lesions. T-cells having specificity for antigens of the invention have demonstrated cytotoxic activity against cells loaded with virally-encoded peptide epitopes, and in many cases, against cells infected with HSV. The identification of immunogenic antigens responsible for T-cell specificity provides improved anti-viral therapeutic and prophylactic strategies. Compositions containing antigens or polynucleotides encoding antigens of the invention provide effectively targeted vaccines for prevention and treatment of HSV infection.

12 Claims, 15 Drawing Sheets

OTHER PUBLICATIONS

C.M. Posavad et al., "High Frequency of CD8+ Cytotoxic T-Lymphoctye Precursors Specific for Herpes Simplex Viruses in Persons with Genital Herpes," Journal of Virology, 1996, 70(11):8165-8168.

S. Reichstetter et al., "MCH-Peptide Ligand Interactions Establish a Functional Threshold for Antigen-Specific T Cell Recognition," Human Immunology, 1999, 60(7):608-618.

B. Roizman et al., "Herpes Simplex Viruses and Their Replication", Fundamental Virology, 2nd Edition, ed. Fields et al, Raven Press, 1991, New York, pp. 849-895.

Tatman, J.D. et al., "Assembly of Herpes Simplex Virus Type 1 Using a Panel of Recombinant Baculoviruses," Journal of General Virology, 1994, 75, 1101-1113.

M.A. Tigges et al., "Human CD8* Herpes Simplex Virus-Specific Cytotoxic T-Lymphocyte Clones Recognize Diverse Virion Protein Antigens," Journal of Virology, 1992, 66(3):1622-1634.

Williams et al., "Characterization of a Herpes Simplex Virus Type 2 Deoxyuridine . . . " Virology, 1987, 156:282-292.

* cited by examiner

FIG. 8A
FIG. 8B
FIG. 8C
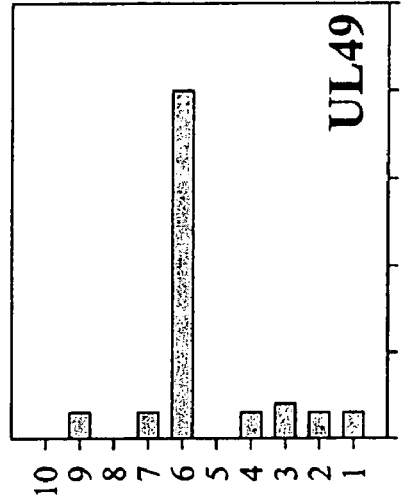
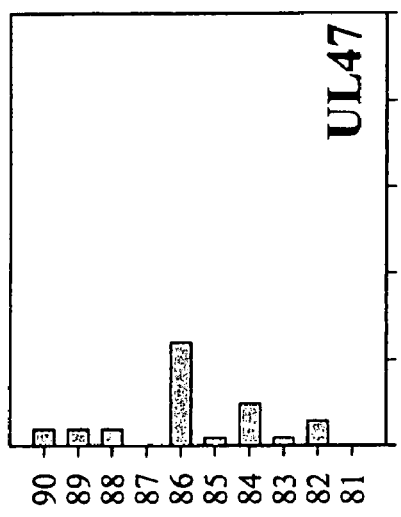
FIG. 8D
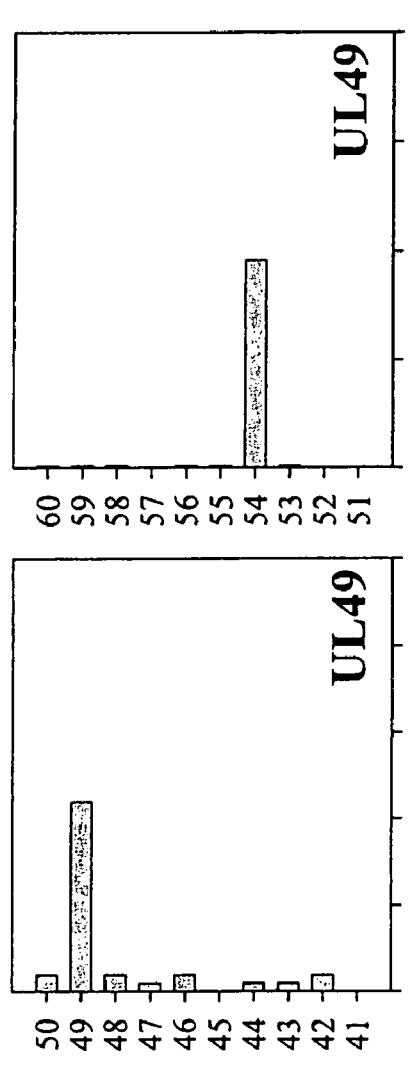
FIG. 8E
** UL49/49-57 epitope B*0702-restricted

SEQUENCE LISTING

<160> NUMBER OF SEQ ID NOS: 32

<210> SEQ ID NO 1
<211> LENGTH: 825
<212> TYPE: PRT
<213> ORGANISM: Herpes simplex virus-2 (HSV-2)

<400> SEQUENCE: 1

Met Glu Pro Arg Pro Gly Thr Ser Ser Arg Ala Asp Pro Gly Pro Glu
 1               5                  10                  15

Arg Pro Pro Arg Gln Thr Pro Gly Thr Gln Pro Ala Ala Pro His Ala
                20                  25                  30

Trp Gly Met Leu Asn Asp Met Gln Trp Leu Ala Ser Ser Asp Ser Glu

-continued

```
                35                  40                  45
Glu Glu Thr Glu Val Gly Ile Ser Asp Asp Leu His Arg Asp Ser
         50                  55                  60
Thr Ser Glu Ala Gly Ser Thr Asp Thr Glu Met Phe Glu Ala Gly Leu
 65                  70                  75                  80
Met Asp Ala Ala Thr Pro Pro Ala Arg Pro Ala Glu Arg Gln Gly
                 85                  90                  95
Ser Pro Thr Pro Ala Asp Ala Gln Gly Ser Cys Gly Gly Pro Val
             100                 105                 110
Gly Glu Glu Glu Ala Glu Ala Gly Gly Gly Asp Val Cys Ala Val
             115                 120                 125
Cys Thr Asp Glu Ile Ala Pro Pro Leu Arg Cys Gln Ser Phe Pro Cys
 130                 135                 140
Leu His Pro Phe Cys Ile Pro Cys Met Lys Thr Trp Ile Pro Leu Arg
 145                 150                 155                 160
Asn Thr Cys Pro Leu Cys Asn Thr Pro Val Ala Tyr Leu Ile Val Gly
             165                 170                 175
Val Thr Ala Ser Gly Ser Phe Ser Thr Ile Pro Ile Val Asn Asp Pro
             180                 185                 190
Arg Thr Arg Val Glu Ala Glu Ala Val Arg Ala Gly Thr Ala Val
             195                 200                 205
Asp Phe Ile Trp Thr Gly Asn Pro Arg Thr Ala Pro Arg Ser Leu Ser
 210                 215                 220
Leu Gly Gly His Thr Val Arg Ala Leu Ser Pro Thr Pro Pro Trp Pro
 225                 230                 235                 240
Gly Thr Asp Asp Glu Asp Asp Asp Leu Ala Asp Val Asp Tyr Val Pro
             245                 250                 255
Pro Ala Pro Arg Arg Ala Pro Arg Gly Gly Gly Ala Gly Ala
             260                 265                 270
Thr Arg Gly Thr Ser Gln Pro Ala Thr Arg Pro Ala Pro Pro Gly
             275                 280                 285
Ala Pro Arg Ser Ser Ser Gly Gly Ala Pro Leu Arg Ala Gly Val
 290                 295                 300
Gly Ser Gly Ser Gly Gly Pro Ala Val Ala Ala Val Val Pro Arg
 305                 310                 315                 320
Val Ala Ser Leu Pro Pro Ala Ala Gly Gly Gly Arg Ala Gln Ala Arg
                 325                 330                 335
Arg Val Gly Glu Asp Ala Ala Ala Glu Gly Arg Thr Pro Pro Ala
             340                 345                 350
Arg Gln Pro Arg Ala Ala Gln Glu Pro Pro Ile Val Ile Ser Asp Ser
             355                 360                 365
Pro Pro Pro Ser Pro Arg Arg Pro Ala Gly Pro Gly Pro Leu Ser Phe
 370                 375                 380
Val Ser Ser Ser Ser Ala Gln Val Ser Ser Gly Pro Gly Gly Gly Gly
 385                 390                 395                 400
Leu Pro Gln Ser Ser Gly Arg Ala Ala Arg Pro Arg Ala Ala Val Ala
                 405                 410                 415
Pro Arg Val Arg Ser Pro Arg Ala Ala Ala Pro Val Val Ser
             420                 425                 430
Ala Ser Ala Asp Ala Ala Gly Pro Ala Pro Pro Ala Val Pro Val Asp
             435                 440                 445
Ala His Arg Ala Pro Arg Ser Arg Met Thr Gln Ala Gln Thr Asp Thr
             450                 455                 460
```

```
Gln Ala Gln Ser Leu Gly Arg Ala Gly Ala Thr Asp Ala Arg Gly Ser
465                 470                 475                 480

Gly Gly Pro Gly Ala Glu Gly Pro Gly Val Pro Arg Gly Thr Asn
            485                 490                 495

Thr Pro Gly Ala Ala Pro His Ala Ala Glu Gly Ala Ala Arg Pro
        500                 505                 510

Arg Lys Arg Arg Gly Ser Asp Ser Gly Pro Ala Ala Ser Ser Ser Ala
        515                 520                 525

Ser Ser Ser Ala Ala Pro Arg Ser Pro Leu Ala Pro Gln Gly Val Gly
    530                 535                 540

Ala Lys Arg Ala Ala Pro Arg Arg Ala Pro Asp Ser Asp Ser Gly Asp
545                 550                 555                 560

Arg Gly His Gly Pro Leu Ala Pro Ala Ser Ala Gly Ala Ala Pro Pro
            565                 570                 575

Ser Ala Ser Pro Ser Ser Gln Ala Ala Val Ala Ala Ser Ser Ser
            580                 585                 590

Ser Ala Ser Ser Ser Ser Ala Ser Ser Ser Ala Ser Ser Ser Ser
    595                 600                 605

Ala Ser Ser Ser Ala Ser Ser Ser Ala Ser Ser Ser Ala
    610                 615                 620

Ser Ser Ser Ala Gly Gly Ala Gly Gly Ser Val Ala Ser Ala Ser Gly
625                 630                 635                 640

Ala Gly Glu Arg Arg Glu Thr Ser Leu Gly Pro Arg Ala Ala Pro
            645                 650                 655

Arg Gly Pro Arg Lys Cys Ala Arg Lys Thr Arg His Ala Glu Gly Gly
            660                 665                 670

Pro Glu Pro Gly Ala Arg Asp Pro Ala Pro Gly Leu Thr Arg Tyr Leu
        675                 680                 685

Pro Ile Ala Gly Val Ser Ser Val Val Ala Leu Ala Pro Tyr Val Asn
    690                 695                 700

Lys Thr Val Thr Gly Asp Cys Leu Pro Val Leu Asp Met Glu Thr Gly
705                 710                 715                 720

His Ile Gly Ala Tyr Val Leu Val Asp Gln Thr Gly Asn Val Ala
                725                 730                 735

Asp Leu Leu Arg Ala Ala Ala Pro Ala Trp Ser Arg Arg Thr Leu Leu
            740                 745                 750

Pro Glu His Ala Arg Asn Cys Val Arg Pro Pro Asp Tyr Pro Thr Pro
        755                 760                 765

Pro Ala Ser Glu Trp Asn Ser Leu Trp Met Thr Pro Val Gly Asn Met
    770                 775                 780

Leu Phe Asp Gln Gly Thr Leu Val Gly Ala Leu Asp Phe His Gly Leu
785                 790                 795                 800

Arg Ser Arg His Pro Trp Ser Arg Glu Gln Gly Ala Pro Ala Pro Ala
            805                 810                 815

Gly Asp Ala Pro Ala Gly His Gly Glu
        820                 825

<210> SEQ ID NO 2
<211> LENGTH: 490
<212> TYPE: PRT
<213> ORGANISM: Herpes simplex virus-2 (HSV-2)

<400> SEQUENCE: 2

Met Asp Leu Leu Val Asp Asp Leu Phe Ala Asp Ala Asp Gly Val Ser
```

```
              1               5                  10                 15
            Pro Pro Pro Pro Arg Pro Ala Gly Gly Pro Lys Asn Thr Pro Ala Ala
                         20                  25                 30
            Pro Pro Leu Tyr Ala Thr Gly Arg Leu Ser Gln Ala Gln Leu Met Pro
                         35                  40              45
            Ser Pro Met Pro Val Pro Pro Ala Ala Leu Phe Asn Arg Leu Leu
             50                  55                  60
            Asp Asp Leu Gly Phe Ser Ala Gly Pro Ala Leu Cys Thr Met Leu Asp
             65              70                  75                  80
            Thr Trp Asn Glu Asp Leu Phe Ser Gly Phe Pro Thr Asn Ala Asp Met
                         85                  90                  95
            Tyr Arg Glu Cys Lys Phe Leu Ser Thr Leu Pro Ser Asp Val Ile Asp
                         100                 105                110
            Trp Gly Asp Ala His Val Pro Glu Arg Ser Pro Ile Asp Ile Arg Ala
                         115                 120                 125
            His Gly Asp Val Ala Phe Pro Thr Leu Pro Ala Thr Arg Asp Glu Leu
                     130                 135                 140
            Pro Ser Tyr Tyr Glu Ala Met Ala Gln Phe Phe Arg Gly Glu Leu Arg
            145                 150                 155                 160
            Ala Arg Glu Glu Ser Tyr Arg Thr Val Leu Ala Asn Phe Cys Ser Ala
                             165                 170                 175
            Leu Tyr Arg Tyr Leu Arg Ala Ser Val Arg Gln Leu His Arg Gln Ala
                         180                 185                 190
            His Met Arg Gly Arg Asn Arg Asp Leu Arg Glu Met Leu Arg Thr Thr
                         195                 200                 205
            Ile Ala Asp Arg Tyr Tyr Arg Glu Thr Ala Arg Leu Ala Arg Val Leu
                     210                 215                 220
            Phe Leu His Leu Tyr Leu Phe Leu Ser Arg Glu Ile Leu Trp Ala Ala
            225                 230                 235                 240
            Tyr Ala Glu Gln Met Met Arg Pro Asp Leu Phe Asp Gly Leu Cys Cys
                             245                 250                 255
            Asp Leu Glu Ser Trp Arg Gln Leu Ala Cys Leu Phe Gln Pro Leu Met
                         260                 265                 270
            Phe Ile Asn Gly Ser Leu Thr Val Arg Gly Val Pro Val Glu Ala Arg
                     275                 280                 285
            Arg Leu Arg Glu Leu Asn His Ile Arg Glu His Leu Asn Leu Pro Leu
                     290                 295                 300
            Val Arg Ser Ala Ala Glu Glu Pro Gly Ala Pro Leu Thr Thr Pro
            305                 310                 315                 320
            Pro Val Leu Gln Gly Asn Gln Ala Arg Ser Ser Gly Tyr Phe Met Leu
                             325                 330                 335
            Leu Ile Arg Ala Lys Leu Asp Ser Tyr Ser Ser Val Ala Thr Ser Glu
                         340                 345                 350
            Gly Glu Ser Val Met Arg Glu His Ala Tyr Ser Arg Gly Arg Thr Arg
                         355                 360                 365
            Asn Asn Tyr Gly Ser Thr Ile Glu Gly Leu Leu Asp Leu Pro Asp Asp
                     370                 375                 380
            Asp Asp Ala Pro Ala Glu Ala Gly Leu Val Ala Pro Arg Met Ser Phe
            385                 390                 395                 400
            Leu Ser Ala Gly Gln Arg Pro Arg Arg Leu Ser Thr Thr Ala Pro Ile
                             405                 410                 415
            Thr Asp Val Ser Leu Gly Asp Glu Leu Arg Leu Asp Gly Glu Glu Val
                         420                 425                 430
```

```
Asp Met Thr Pro Ala Asp Ala Leu Asp Asp Phe Asp Leu Glu Met Leu
        435                 440                 445

Gly Asp Val Glu Ser Pro Ser Pro Gly Met Thr His Asp Pro Val Ser
        450                 455                 460

Tyr Gly Ala Leu Asp Val Asp Asp Phe Glu Phe Glu Gln Met Phe Thr
465                 470                 475                 480

Asp Ala Met Gly Ile Asp Asp Phe Gly Gly
                485                 490

<210> SEQ ID NO 3
<211> LENGTH: 300
<212> TYPE: PRT
<213> ORGANISM: Herpes simplex virus-2 (HSV-2)

<400> SEQUENCE: 3

Met Thr Ser Arg Arg Ser Val Lys Ser Cys Pro Arg Glu Ala Pro Arg
1               5                   10                  15

Gly Thr His Glu Glu Leu Tyr Tyr Gly Pro Val Ser Pro Ala Asp Pro
            20                  25                  30

Glu Ser Pro Arg Asp Asp Phe Arg Gly Ala Gly Pro Met Arg Ala
        35                  40                  45

Arg Pro Arg Gly Glu Val Arg Phe Leu His Tyr Asp Glu Ala Gly Tyr
    50                  55                  60

Ala Leu Tyr Arg Asp Ser Ser Asp Asp Glu Ser Arg Asp Thr
65                  70                  75                  80

Ala Arg Pro Arg Arg Ser Ala Ser Val Ala Gly Ser His Gly Pro Gly
                85                  90                  95

Pro Ala Arg Ala Pro Pro Pro Gly Gly Pro Val Gly Ala Gly Gly
            100                 105                 110

Arg Ser His Ala Pro Pro Ala Arg Thr Pro Lys Met Thr Arg Gly Ala
            115                 120                 125

Pro Lys Ala Ser Ala Thr Pro Ala Thr Asp Pro Ala Arg Gly Arg Arg
        130                 135                 140

Pro Ala Gln Ala Asp Ser Ala Val Leu Leu Asp Ala Pro Ala Pro Thr
145                 150                 155                 160

Ala Ser Gly Arg Thr Lys Thr Pro Ala Gln Gly Leu Ala Lys Lys Leu
                165                 170                 175

His Phe Ser Thr Ala Pro Pro Ser Pro Thr Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Thr His Ala Arg Leu Ala Ala Val Gln Leu Trp Asp Met Ser
    210                 215                 220

Arg Pro His Thr Asp Glu Asp Leu Asn Glu Leu Leu Asp Leu Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Ala Ala Gln Asp Val Asp Ala Thr Ala Ala
            260                 265                 270

Ala Arg Gly Arg Pro Ala Gly Arg Ala Ala Thr Ala Arg Ala Pro
        275                 280                 285

Ala Arg Ser Ala Ser Arg Pro Arg Arg Pro Leu Glu
    290                 295                 300
```

<210> SEQ ID NO 4
<211> LENGTH: 21
<212> TYPE: PRT
<213> ORGANISM: Herpes simplex virus-2 (HSV-2)

<400> SEQUENCE: 4

Gly Gly Pro Val Gly Ala Gly Gly Arg Ser His Ala Pro Ala Arg Thr
 1               5                  10                  15

Pro Lys Met Thr Arg
            20

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
ggaagatcta cctctcgccg ctccgtca                                          28

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
ccggaattct tgtctgtcgt ctgaacgcg                                         29

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
tgctctagag actcgatccc tgcgcgtcgg                                        30

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
taaggtacct gaaccccggc ccggcacgag c                                      31

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
tgctctagac caggcgtgcg gggcggcggg                                        30

<210> SEQ ID NO 10
<211> LENGTH: 27
<212> TYPE: DNA
<213> ORGANISM: Artificial Sequence
<220> FEATURE:

-continued

```
<223> OTHER INFORMATION: primer

<400> SEQUENCE: 10
ctaggatccc ctccggccac catgtcc                                          27

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
cgatctagac ctatgggcgt ggcgggc                                          27

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
cgaggatccg tctccgccat gcaacgccg                                        29

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
cgctctagat tttaatggct ctggtgtcg                                        29

<210> SEQ ID NO 14
<211> LENGTH: 10
<212> TYPE: PRT
<213> ORGANISM: Artificial Sequence
<220> FEATURE:
<223> OTHER INFORMATION: epitope

<400> SEQUENCE: 14

Ala Glu Glu Ala Ala Gly Ile Gly Ile Leu
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: epitope

<400> SEQUENCE: 15

Gly Ala Glu Thr Phe Tyr Val Asp Gly Ala
 1               5                  10

<210> SEQ ID NO 16
<211> LENGTH: 15
<212> TYPE: PRT
<213> ORGANISM: Herpes simplex virus-2 (HSV-2)

<400> SEQUENCE: 16

Ala Ile Asp Tyr Val His Cys Lys Gly Ile Ile His Arg Asp Ile
 1               5                  10                  15
```

```
<210> SEQ ID NO 17
<211> LENGTH: 15
<212> TYPE: PRT
<213> ORGANISM: Herpes simplex virus-1 (HSV-1)

<400> SEQUENCE: 17

Ala Val Asp Tyr Ile His Arg Gln Gly Ile Ile His Arg Asp Ile
 1               5                  10                  15

<210> SEQ ID NO 18
<211> LENGTH: 15
<212> TYPE: PRT
<213> ORGANISM: Herpes simplex virus-2 (HSV-2)

<400> SEQUENCE: 18

Ala Val Pro Leu Leu Ser Ala Gly Gly Ala Ala Pro Pro His Pro
 1               5                  10                  15

<210> SEQ ID NO 19
<211> LENGTH: 15
<212> TYPE: PRT
<213> ORGANISM: Herpes simplex virus-1 (HSV-1)

<400> SEQUENCE: 19

Ala Val Pro Leu Leu Ser Ala Gly Gly Leu Val Ser Pro Gln Ser
 1               5                  10                  15

<210> SEQ ID NO 20
<211> LENGTH: 15
<212> TYPE: PRT
<213> ORGANISM: Herpes simplex virus-2 (HSV-2)

<400> SEQUENCE: 20

Glu Leu Tyr Tyr Gly Pro Val Ser Pro Ala Asp Pro Glu Ser Pro
 1               5                  10                  15

<210> SEQ ID NO 21
<211> LENGTH: 16
<212> TYPE: PRT
<213> ORGANISM: Herpes simplex virus-1 (HSV-1)

<400> SEQUENCE: 21

Asp Leu Tyr Tyr Thr Pro Ser Ser Gly Met Ala Ser Pro Asp Ser Pro
 1               5                  10                  15

<210> SEQ ID NO 22
<211> LENGTH: 15
<212> TYPE: PRT
<213> ORGANISM: Herpes simplex virus-2 (HSV-2)

<400> SEQUENCE: 22

Pro Met Arg Ala Arg Pro Arg Gly Glu Val Arg Phe Leu His Tyr
 1               5                  10                  15

<210> SEQ ID NO 23
<211> LENGTH: 15
<212> TYPE: PRT
<213> ORGANISM: Herpes simplex virus-1 (HSV-1)

<400> SEQUENCE: 23

Gln Arg Ser Ala Arg Gln Arg Gly Glu Val Arg Phe Val Gln Tyr
 1               5                  10                  15

<210> SEQ ID NO 24
```

```
<211> LENGTH: 15
<212> TYPE: PRT
<213> ORGANISM: Herpes simplex virus-2 (HSV-2)

<400> SEQUENCE: 24

Arg Pro Arg Gly Glu Val Arg Phe Leu His Tyr Asp Glu Ala Gly
1               5                   10                  15

<210> SEQ ID NO 25
<211> LENGTH: 15
<212> TYPE: PRT
<213> ORGANISM: Herpes simplex virus-1 (HSV-1)

<400> SEQUENCE: 25

Arg Gln Arg Gly Glu Val Arg Phe Val Gln Tyr Pro Glu Ser Asp
1               5                   10                  15

<210> SEQ ID NO 26
<211> LENGTH: 15
<212> TYPE: PRT
<213> ORGANISM: Herpes simplex virus-2 (HSV-2)

<400> SEQUENCE: 26

Val Ala Gly Phe Asn Lys Arg Val Phe Cys Ala Ala Val Gly Arg
1               5                   10                  15

<210> SEQ ID NO 27
<211> LENGTH: 15
<212> TYPE: PRT
<213> ORGANISM: Herpes simplex virus-1 (HSV-1)

<400> SEQUENCE: 27

Val Ala Gly Phe Asn Lys Arg Val Phe Cys Ala Ala Val Gly Arg
1               5                   10                  15

<210> SEQ ID NO 28
<211> LENGTH: 16
<212> TYPE: PRT
<213> ORGANISM: Herpes simplex virus-2 (HSV-2)

<400> SEQUENCE: 28

Ser Thr Ala Pro Glu Val Gly Thr Tyr Thr Pro Leu Arg Tyr Ala Cys
1               5                   10                  15

<210> SEQ ID NO 29
<211> LENGTH: 16
<212> TYPE: PRT
<213> ORGANISM: Herpes simplex virus-1 (HSV-1)

<400> SEQUENCE: 29

Phe Thr Ala Pro Glu Val Gly Thr Tyr Thr Pro Leu Arg Tyr Ala Cys
1               5                   10                  15

<210> SEQ ID NO 30
<211> LENGTH: 14
<212> TYPE: PRT
<213> ORGANISM: Herpes simplex virus-2 (HSV-2)

<400> SEQUENCE: 30

Ala Glu Arg Gln Gly Ser Pro Thr Pro Ala Asp Ala Gln Gly
1               5                   10

<210> SEQ ID NO 31
<211> LENGTH: 10
<212> TYPE: PRT
```

```
-continued

<213> ORGANISM: Herpes simplex virus-2 (HSV-2)

<400> SEQUENCE: 31

Ala Glu Arg Gln Gly Ser Pro Thr Thr Pro
 1               5                  10

<210> SEQ ID NO 32
<211> LENGTH: 20
<212> TYPE: PRT
<213> ORGANISM: Herpes simplex virus-2 (HSV-2)

<400> SEQUENCE: 32

Arg Leu Arg Glu Leu Asn His Ile Arg Glu His Leu Asn Leu Pro Leu
 1               5                  10                  15

Val Arg Ser Ala
            20
```

IMMUNOLOGICALLY SIGNIFICANT HERPES SIMPLEX VIRUS ANTIGENS AND METHODS FOR USING SAME This application is a divisional of application Ser. No. 10/210,428, filed Jul. 31, 2002, now U.S. Pat. No. 6,814,969, issued Nov. 9, 2004 which claims the benefit of U.S. provisional patent applications No. 60/308,923, filed Jul. 31, 2001, and No. 60/309,428, filed Aug. 1, 2001, the entire contents of each of which are incorporated herein by reference.

This application is related to U.S. patent applications Ser. No. 09/672,595, filed Sep. 28, 2000, now U.S. Pat. No. 6,413,518, issued Jul. 2, 2002, and Ser. No. 09/368,770, filed Aug. 5, 1999, now U.S. Pat. No. 6,375,952, issued Apr. 23, 2002, and to U.S. provisional patent applications No. 60/095,724, filed Aug. 7, 1998, 60/157,181, filed Sep. 30, 1999, No. 60/203,660, filed May 12, 2000, and No. 60/218,104, filed Jul. 13, 2000, the entire contents of each of which are incorporated herein by reference. Throughout this application various publications are referenced. The disclosures of these publications in their entireties are hereby incorporated by reference into this application in order to describe more fully the state of the art to which this invention pertains.

TECHNICAL FIELD OF THE INVENTION

The invention relates to molecules, compositions and methods that can be used for the treatment and prevention of HSV infection. More particularly, the invention identifies epitopes of HSV proteins that can be used for methods, molecules and compositions having the antigenic specificity of HSV-specific T cells, and in particular, of CD8+ as well as CD4+ T cells.

BACKGROUND OF THE INVENTION

Cellular immune responses are required to limit the severity of recurrent HSV infection in humans. Initial genital HSV-2 infections are prolonged and severe, while recurrences are less severe and more frequently asymptomatic. Resolution of primary HSV-2 infection is associated with infiltration of antigen-specific T cells, including CD8+ cytotoxic T lymphocytes (CTLs). Serial lesion biopsy studies of recurrent HSV-2 infection in humans has shown a shift to CD8+ predominance as lesions mature and correlation of local CTL activity with virus clearance (Koelle, DM et al., J. Clin. Invest. 1998, 101:1500–1508; Cunningham, AL et al., J. Clin. Invest. 1985, 75:226–233). Thus, HSV antigens recognized by CD8+ CTL can be used for novel therapies and vaccines.

The complete DNA sequence of herpes simplex virus (HSV) is approximately 150 kb and encodes about 85 known genes, each of which encodes a protein in the range of 50–1000 amino acids in length. Unknown are the immunogenic epitopes within these proteins, each epitope approximately 9–12 amino acids in length, that are capable of eliciting an effective T cell immune response to viral infection.

There remains a need to identify specific epitopes capable of eliciting an effective immune response to HSV infection. Such information can lead to the identification of more effective immunogenic antigens useful for the prevention and treatment of HSV infection.

SUMMARY OF THE INVENTION

The invention provides HSV antigens, polypeptides comprising HSV antigens, polynucleotides encoding the polypeptides, vectors, and recombinant viruses containing the polynucleotides, antigen-presenting cells (APCs) presenting the polypeptides, immune cells directed against HSV, and pharmaceutical compositions. The pharmaceutical compositions can be used both prophylactically and therapeutically. The antigens of the invention are recognized by T cells recovered from herpetic lesions. The invention additionally provides methods, including methods for preventing and treating HSV infection, for killing HSV-infected cells, for inhibiting viral replication, for enhancing secretion of antiviral and/or immunomodulatory lymphokines, and for enhancing production of HSV-specific antibody. For preventing and treating HSV infection, for enhancing secretion of antiviral and/or immunomodulatory lymphokines, for enhancing production of HSV-specific antibody, and generally for stimulating and/or augmenting HSV-specific immunity, the method comprises administering to a subject a polypeptide, polynucleotide, recombinant virus, APC, immune cell or composition of the invention. The methods for killing HSV-infected cells and for inhibiting viral replication comprise contacting an HSV-infected cell with an immune cell of the invention. The immune cell of the invention is one that has been stimulated by an antigen of the invention or by an APC that presents an antigen of the invention. A method for producing such immune cells is also provided by the invention. The method comprises contacting an immune cell with an APC, preferably a dendritic cell, that has been modified to present an antigen of the invention. In a preferred embodiment, the immune cell is a T cell such as a CD4+ or CD8+ T cell.

In one embodiment, the invention provides a composition comprising an HSV polypeptide. In one embodiment, the polypeptide comprises a $U_L 49$ protein or a fragment thereof. In a preferred embodiment, the fragment of a $U_L 49$ protein comprises amino acids 14–22, 21–35, 45–59, 49–57, 49–63, 105–190, 177–220 or 193–208 of $U_L 49$ or variant thereof. In another embodiment, the polypeptide comprises an ICP0 protein or a fragment thereof. In one embodiment, the fragment of an ICP0 protein comprises amino acids 92–101, 92–105, 288–307 or 743–751 of ICP0 or a substitutional variant thereof. In another embodiment, the polypeptide comprises a $U_L 48$ protein or a fragment thereof. In one embodiment, the fragment of a $U_L 48$ protein comprises amino acids 185–197, 209–221, 288–307 or 430–449 of VP16 ($U_L 48$) or a substitutional variant thereof.

Also provided is an isolated polynucleotide that encodes a polypeptide of the invention, and a composition comprising the polynucleotide. The invention additionally provides a recombinant virus genetically modified to express a polynucleotide of the invention, and a composition comprising the recombinant virus. In preferred embodiments, the virus is a vaccinia virus, canary pox virus, HSV, lentivirus, retrovirus or adenovirus. A composition of the invention can be a pharmaceutical composition. The composition can optionally comprise a pharmaceutically acceptable carrier and/or an adjuvant.

BRIEF DESCRIPTION OF THE FIGURES

FIGS. 8A–E show the HLA types of the donors used in Example 5.

DETAILED DESCRIPTION OF THE INVENTION

Figures 1A, 1B:
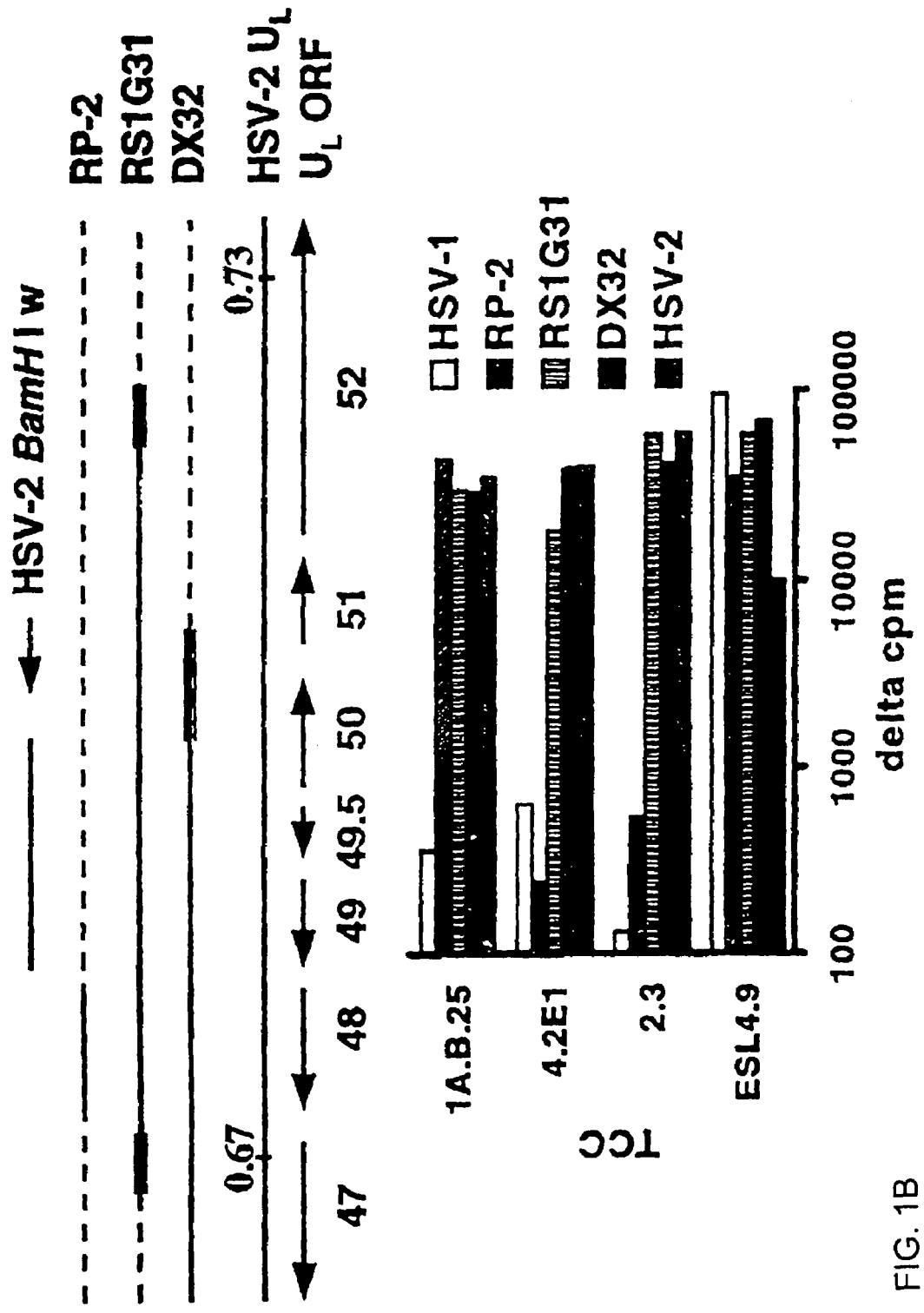
FIG. 1A is a schematic representing organization of the HSV genome in the region of 0.67–0.73 map units. Boundaries are approximate. HSV-1×HSV-2 intertypic recombinant viruses (IRV) are also shown. HSV-2 DNA is indicated by a solid line; HSV-1 DNA by a dashed line, and indeterminate regions by a multiple line. The HSV-2 BamH I w fragment used for expression cloning is also shown.
FIG. 1B is a bar graph showing proliferative responses of T-cell clones (TCC) to the indicated IRV. Data are delta CPM [$^3$H] thymidine incorporation compared to media alone, which was less than 500 cpm in each case.

The invention provides HSV antigens that are useful for the prevention and treatment of HSV infection. Disclosed herein are antigens and/or their constituent epitopes confirmed to be recognized by T-cells derived from herpetic lesions. In some embodiments, T-cells having specificity for antigens of the invention have demonstrated cytotoxic activity against virally infected cells. The identification of immunogenic antigens responsible for T-cell specificity facilitates the development of improved anti-viral therapeutic and prophylactic strategies. Compositions containing antigens or polynucleotides encoding antigens of the invention provide effectively targeted vaccines for prevention and treatment of HSV infection.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids, and preferably at least about 15 amino acids.

As used herein, "HSV polypeptide" includes HSV-1 and HSV-2, unless otherwise indicated. References to amino acids of HSV proteins or polypeptides are based on the genomic sequence information regarding HSV-2 as described in A. Dolan et al., 1998, J. Virol. 72(3):2010–2021. As noted below, the predicted polypeptide sequence of ICP0 of HSV-2 based on sequencing RNA from cells transfected with a fragment of ICP0 differs from the published sequence by the omission of amino acid Q26.

As used herein, "substitutional variant" refers to a molecule having one or more amino acid substitutions or deletions in the indicated amino acid sequence, yet retaining the ability to be specifically recognized by an immune cell. The amino acid sequence of a substitutional variant is preferably at least 80% identical to the native amino acid sequence, or more preferably, at least 90% identical to the native amino acid sequence. Typically, the substitution is a conservative substitution. One method for determining whether a molecule can be specifically recognized by an immune cell is the cytotoxicity assay described in D. M. Koelle et al., 1997, Human Immunol. 53:195–205. Other methods for determining whether a molecule can be specifically recognized by an immune cell are described in the examples provided hereinbelow, including the ability to stimulate secretion of interferon-gamma or the ability to lyse cells presenting the molecule. An immune cell will specifically recognize a molecule when, for example, stimulation with the molecule results in secretion of greater interferon-gamma than stimulation with control molecules. For example, the molecule may stimulate greater than 5 pg/ml, or preferably greater than 10 pg/ml, interferon-gamma secretion, whereas a control molecule will stimulate less than 5 pg/ml interferon-gamma.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, furmaric acid, gluconic acid, citric acid, malic acid, ascorbic acid, benzoic acid, tannic acid, pamoic acid, alginic acid, polyglutamic acid, naphthalenesulfonic acids, naphthalene-disulfonic acids, polygalacturonic acid; (b) salts with poly-valent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences,* 18th edition, A. Gennaro, ed., Mack Publishing Co., Easton, Pa., 1990).

As used herein, "adjuvant" includes those adjuvants commonly used in the art to facilitate the stimulation of an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (Smith-Kline Beecham); QS-21 (Aquilla); MPL or 3d-MPL (Corixa Corporation, Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

As used herein, to "prevent" or "protect against" a condition or disease means to hinder, reduce or delay the onset or progression of the condition or disease.

HSV Polypeptides

In one embodiment, the invention provides an isolated herpes simplex virus (HSV) polypeptide. The polypeptide comprises an ICP0, VP16 ($U_L48$), or $U_L49$ protein or a fragment thereof. In one embodiment, the fragment comprises amino acids 92–101, 92–105, 288–307 or 743–751 of ICP0 or a substitutional variant thereof. In other embodiments, the fragment comprises amino acids 185–197, 209–221, 288–307, 430–449 or 437–449 of VP16 ($U_L48$) or a substitutional variant thereof. In another embodiment, the fragment comprises amino acids 14–22, 21–35, 45–59, 47–55, 49–57, 49–63, 105–190, 177–220 or 193–208 of $U_L49$ or a substitutional variant thereof. The reference to amino acid residues is made with respect to the proteins of the HSV-2 genome as described in A. Dolan et al., 1998, J. Virol. 72(3):2010–2021. The amino acid sequences of ICP0, VP16 ($U_L48$), and $U_L49$ are as follows.

```
        ICP0 amino acid sequence (SEQ ID NO: 1)
  1 meprpgtssr adpgperppr qtpgtqpaap hawgmlndmq wlassdseee tevgisdddl 61 hrdstseags tdtemfeagl mdaatpparp paerqgsptp adaqgscggg pvgeeeaeag 121 gggdvcavct deiapplrcq sfpclhpfci pcmktwiplr ntcplcntpv aylivgvtas 181 gsfstipivn dprtrveaea avragtavdf iwtgnprtap rslslgghtv ralsptppwp 241 gtddedddla dvdyvppapr raprrgggga gatrgtsqpa atrpappgap rsssggapl 301 ragvgsgsgg gpavaavvpr vaslppaagg graqarrvge daaaaegrtp parqpraaqe 361 ppivisdspp psprrpagpg plsfvssssa qvssgpgggg lpqssgraar praavaprvr 421 sppraaaapv vsasadaagp appavpvdah raprsrmtqa qtdtqaqslg ragatdargs 481 ggpgaeggpg vprgtntpga aphaaegaaa rprkrrgsds gpaasssass saaprsplap 541 qgvgakraap rrapdsdsgd rghgplapas agaappsasp ssqaavaaas sssasssas 601 sssassssas sssassssas sssasssagg aggsvasasg agerretslg praaaprgpr 661 kcarktrhae ggpepgardp apgltrylpi agvssvvala pyvnktvtgd clpvldmetg 721 higayvvlvd qtgnvadllr aaapawsrrt llpeharncv rppdyptppa sewnslwmtp 781 vgnmlfdqgt lvgaldfhgl rsrhpwsreq gapapagdap aghge VP16 ($U_L48$) amino acid sequence (SEQ ID NO: 2)
  1 mdllvddlfa dadgvspppp rpaggpkntp aapplyatgr lsqaqlmpsp pmpvppaalf 61 nrllddlgfs agpalctmld twnedlfsgf ptnadmyrec kflstlpsdv idwgdahvpe 121 rspidirahg dvafptlpat rdelpsyyea maqffrgelr areesyrtvl anfcsalyry 181 lrasvrqlhr qahmrgrnrd lremlrttia dryyretarl arvlflhlyl flsreilwaa 241 yaeqmmrpdl fdglccdles wrqlaclfqp lmfingsltv rgvpvearrl reinhirehi 301 nlplvrsaaa eepgaplttp pvlqgnqars sgyfmllira kldsyssvat segesvmreh 361 aysrgrtrnn ygstieglld lpddddapae aglvaprmsf lsagqrprrl sttapitdvs 421 lgdelrldge evdmtpadal ddfdlemlgd vespspgmth dpvsygaldv ddfefeqmft 481 damgiddfgg $U_L$ amino acid sequence (SEQ ID NO: 3)
  1 mtsrrsvksc preaprgthe elyygpvspa dpesprddfr rgagpmrarp rgevrflhyd 61 eagyalyrds ssdddesrdt arprrsasva gshgpgpara ppppggpvga ggrshappar 121 tpkmtrgapk asatpatdpa rgrrpaqads avildapapt asgrtktpaq glakklhfst 181 appsptapwt prvagfnkrv fcaavgrlaa tharlaavql wdmsrphtde dlnellditt 241 irvtvcegkn llqranelvn pdaaqdvdat aaargrpagr aaatarapar sasrprrple
```

The polypeptide can be a fusion protein. In one embodiment, the fusion protein is soluble. A soluble fusion protein of the invention can be suitable for injection into a subject and for eliciting an immune response. Within certain embodiments, a polypeptide can be a fusion protein that comprises multiple polypeptides as described herein, or that comprises at least one polypeptide as described herein and an unrelated sequence. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., 1985, Gene 40:39–46; Murphy et al., 1986, Proc. Natl. Acad. Sci. USA 83:8258–8262; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al., 1997, New Engl. J. Med., 336:86–9).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenza virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265–292,1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In some embodiments, it may be desirable to couple a therapeutic agent and a polypeptide of the invention, or to couple more than one polypeptide of the invention. For example, more than one agent or polypeptide may be coupled directly to a first polypeptide of the invention, or linkers that provide multiple sites for attachment can be used. Alternatively, a carrier can be used. Some molecules are particularly suitable for intercellular trafficking and protein delivery, including, but not limited to, VP22 (Elliott and O'Hare, 1997, Cell 88:223–233; see also Kim et al., 1997, J. Immunol. 159:1666–1668; Rojas et al., 1998, Nature Biotechnology 16:370; Kato et al., 1998, FEBS Lett. 427(2):203–208; Vives et al., 1997, J. Biol. Chem. 272(25): 16010–7; Nagahara et al., 1998, Nature Med. 4(12):1449–1452).

A carrier may bear the agents or polypeptides in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088).

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not part of the natural environment.

The polypeptide can be isolated from its naturally occurring form, produced by recombinant means or synthesized chemically. Recombinant polypeptides encoded by DNA sequences described herein can be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably the host cells employed are E. coli/, yeast or a mammalian cell line such as Cos or CHO. Supernatants from the soluble host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Fragments and other variants having less than about 100 amino acids, and generally less than about 50 ammo acids, may also be generated by synthetic means, using techniques well known to those of ordinary skill in the art. For example, such polypeptides may be synthesized using any of the commercially available solid-phase techniques, such as the Merrifield solid-phase synthesis method, wherein amino acids are sequentially added to a growing amino acid chain (Merrifield, 1963, J. Am. Chem. Soc. 85:2146–2149). Equipment for automated synthesis of polypeptides is commercially available from suppliers such as Perkin Elmer/ Applied BioSystems Division (Foster City, Calif.), and may be operated according to the manufacturer's instructions.

Variants of the polypeptide for use in accordance with the invention can have one or more amino acid substitutions, deletions, additions and/or insertions in the amino acid sequence indicated that result in a polypeptide that retains the ability to elicit an immune response to HSV or HSV-infected cells. Such variants may generally be identified by modifying one of the polypeptide sequences described herein and evaluating the reactivity of the modified polypeptide using a known assay such as a T cell assay described herein. Polypeptide variants preferably exhibit at least about 70%, more preferably at least about 90%, and most preferably at least about 95% identity to the identified polypeptides. These amino acid substitutions include, but are not necessarily limited to, amino acid substitutions known in the art as "conservative".

A "conservative" substitution is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

One can readily confirm the suitability of a particular variant by assaying the ability of the variant polypeptide to elicit an immune response. The ability of the variant to elicit an immune response can be compared to the response elicited by the parent polypeptide assayed under identical circumstances. One example of an immune response is a cellular immune response. The assaying can comprise performing an assay that measures T cell stimulation or activation. Examples of T cells include CD4 and CD8 T cells.

One example of a T cell stimulation assay is a cytotoxicity assay, such as that described in Koelle, DM et al., Human Immunol. 1997, 53;195–205. In one example, the cytotoxicity assay comprises contacting a cell that presents the antigenic viral peptide in the context of the appropriate HLA molecule with a T cell, and detecting the ability of the T cell to kill the antigen presenting cell. Cell killing can be detected by measuring the release of radioactive $^{51}$Cr from the antigen presenting cell. Release of $^{51}$Cr into the medium from the antigen presenting cell is indicative of cell killing. An exemplary criterion for increased killing is a statistically significant increase in counts per minute (cpm) based on counting of $^{51}$Cr radiation in media collected from antigen presenting cells admixed with T cells as compared to control media collected from antigen presenting cells admixed with media.

Polynucleotides, Vectors, Host Cells and Recombinant Viruses

The invention provides polynucleotides that encode one or more polypeptides of the invention. The complete genome sequence of HSV-2, strain HG52, can be found on the NCBI web site (www.ncbi.nih.gov), Accession No. Z86099. The polynucleotide can be included in a vector. The vector can further comprise an expression control sequence operably linked to the polynucleotide of the invention. In some embodiments, the vector includes one or more polynucleotides encoding other molecules of interest. In one embodiment, the polynucleotide of the invention and an additional polynucleotide can be linked so as to encode a fusion protein.

Within certain embodiments, polynucleotides may be formulated so to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

The invention also provides a host cell transformed with a vector of the invention. The transformed host cell can be used in a method of producing a polypeptide of the invention. The method comprises culturing the host cell and recovering the polypeptide so produced. The recovered polypeptide can be purified from culture supernatant.

Vectors of the invention can be used to genetically modify a cell, either in vivo, ex vivo or in vitro. Several ways of genetically modifying cells are known, including transduction or infection with a viral vector either directly or via a retroviral producer cell, calcium phosphate precipitation, fusion of the recipient cells with bacterial protoplasts containing the DNA, treatment of the recipient cells with liposomes or microspheres containing the DNA, DEAE dextran, receptor-mediated endocytosis, electroporation, micro-injection, and many other techniques known to those of skill. See, e.g., Sambrook et al. Molecular Cloning—A Laboratory Manual (2nd ed.) 1–3, 1989; and Current Protocols in Molecular Biology, F. M. Ausubel et al., eds., Greene Publishing Associates, Inc. and John Wiley & Sons, Inc., (1994 Supplement).

Examples of viral vectors include, but are not limited to retroviral vectors based on, e.g., HIV, SIV, and murine retroviruses, gibbon ape leukemia virus and other viruses such as adeno-associated viruses (AAVs) and adenoviruses. (Miller et al. 1990, Mol. Cell Biol. 10:4239; J. Kolberg 1992, NIH Res. 4:43, and Cornetta et al. 1991, Hum. Gene Ther. 2:215). Widely used retroviral vectors include those based upon murine leukemia virus (MuLV), gibbon ape leukemia virus (GaLV), ecotropic retroviruses, simian immunodeficiency virus (SIV), human immunodeficiency virus (HIV), and combinations. See, e.g. Buchscher et al. 1992, J. Virol. 66(5):2731–2739; Johann et al. 1992, J. Virol. 66(5):1635–1640; Sommerfelt et al. 1990, Virol. 176:58–59; Wilson et al. 1989, J. Virol. 63:2374–2378; Miller et al. 1991, J. Virol. 65:2220–2224, and Rosenberg and Fauci 1993 in Fundamental Immunology, Third Edition, W. E. Paul (ed.) Raven Press, Ltd., New York and the references therein; Miller et al. 1990, Mol. Cell. Biol. 10:4239; R. Kolberg 1992, J. NIH Res. 4:43; and Cornetta et al. 1991, Hum. Gene Ther. 2:215.

In vitro amplification techniques suitable for amplifying sequences to be subcloned into an expression vector are known. Examples of such in vitro amplification methods, including the polymerase chain reaction (PCR), ligase chain reaction (LCR), Qβ-replicase amplification and other RNA polymerase mediated techniques (e.g., NASBA), are found in Sambrook et al. 1989, Molecular Cloning—A Laboratory Manual (2nd Ed) 1–3; and U.S. Pat. No. 4,683,202; PCR Protocols A Guide to Methods and Applications (Innis et al. eds.) Academic Press Inc. San Diego, Calif. 1990. Improved methods of cloning in vitro amplified nucleic acids are described in U.S. Pat. No. 5,426,039.

The invention additionally provides a recombinant microorganism genetically modified to express a polynucleotide of the invention. The recombinant microorganism can be useful as a vaccine, and can be prepared using techniques known in the art for the preparation of live attenuated vaccines. Examples of microorganisms for use as live vaccines include, but are not limited to, viruses and bacteria. In a preferred embodiment, the recombinant microorganism is a virus. Examples of suitable viruses include, but are not limited to, vaccinia virus, canary pox virus, retrovirus, lentivirus, HSV and adenovirus.

Compositions

The invention provides compositions that are useful for treating and preventing HSV infection. The compositions can be used to inhibit viral replication and to kill virally-infected cells. In one embodiment, the composition is a pharmaceutical composition. The composition can comprise a therapeutically or prophylactically effective amount of a polypeptide, polynucleotide, recombinant virus, APC or immune cell of the invention. An effective amount is an amount sufficient to elicit or augment an immune response, e.g., by activating T cells. One measure of the activation of T cells is a cytotoxicity assay, as described in D. M. Koelle et al., 1997, Human Immunol. 53:195–205. In some embodiments, the composition is a vaccine.

The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions.

The composition of the invention can further comprise one or more adjuvants. Examples of adjuvants include, but are not limited to, helper peptide, alum, Freund's, muramyl tripeptide phosphatidyl ethanolamine or an immunostimulating complex, including cytokines. In some embodiments, such as with the use of a polynucleotide vaccine, an adjuvant such as a helper peptide or cytokine can be provided via a polynucleotide encoding the adjuvant. Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other viral antigens may be present, either incorporated into a fusion polypeptide or as a separate compound, within the composition or vaccine.

A pharmaceutical composition or vaccine may contain DNA encoding one or more of the polypeptides of the invention, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, 1998, Crit. Rev. Therap. Drug Carrier Systems 15:143–198, and references cited therein. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., 1989, Proc. Natl. Acad. Sci. USA 86:317–321; Flexner et al., 1989, Ann. My Acad. Sci. 569:86–103; Flexner et al., 1990, Vaccine 8:17–21; U.S. Pat. Nos. 4,603,112, 4,769,330, and 5,017,487; WO 89/01973; U.S. Pat. No. 4,777,127; GB 2,200,651; EP 0,345,242; WO 91102805; Berkner, 1988, Biotechniques 6:616–627; Rosenfeld et al., 1991, Science 252:431–434; Kolls et al., 1994, Proc. Natl. Acad. Sci. USA 91:215–219; Kass-Eisler et al., 1993, Proc. Natl. Acad. Sci. USA 90:11498–11502; Guzman et al., 1993, Circulation 88:2838–2848; and Guzman et al., 1993, Cir. Res. 73:1202–1207. Techniques for incorporating DNA into such expression systems are well known to those of ordinary skill in the art. The DNA may also be "naked," as described, for example, in Ulmer et al., 1993, Science 259:1745–1749 and reviewed by Cohen, 1993, Science 259:1691–1692. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N. J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, 1989, Ann. Rev. Immunol. 7:145–173.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL™ adjuvants are available from Corixa Corporation (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Another adjuvant that may be used is AS-2 (Smith-Kline Beecham). Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets HSV-infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have antiviral effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic immunity (see Timmerman and Levy, Ann. Rev. Med. 50:507–529,1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (Zitvogel et al., 1998, Nature Med. 4:594–600).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well-characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86). APCs may generally be transfected with a polynucleotide encoding a polypeptide (or portion or other variant thereof) such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., 1997, Immunology and Cell Biology 75:456–460. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Administration of the Compositions

Treatment includes prophylaxis and therapy. Prophylaxis or treatment can be accomplished by a single direct injection at a single time point or multiple time points. Administration can also be nearly simultaneous to multiple sites. Patients or subjects include mammals, such as human, bovine, equine, canine, feline, porcine, and ovine animals. Preferably, the patients or subjects are human.

Compositions are typically administered in vivo via parenteral (e.g. intravenous, subcutaneous, and intramuscular) or other traditional direct routes, such as buccal/sublingual, rectal, oral, nasal, topical, (such as transdermal and ophthalmic), vaginal, pulmonary, intraarterial, intraperitoneal, intraocular, or intranasal routes or directly into a specific tissue.

The compositions are administered in any suitable manner, often with pharmaceutically acceptable carriers. Suitable methods of administering cells in the context of the present invention to a patient are available, and, although more than one route can be used to administer a particular cell composition, a particular route can often provide a more immediate and more effective reaction than another route.

The dose administered to a patient, in the context of the present invention should be sufficient to effect a beneficial therapeutic response in the patient over time, or to inhibit infection or disease due to infection. Thus, the composition is administered to a patient in an amount sufficient to elicit an effective immune response to the specific antigens and/or to alleviate, reduce, cure or at least partially arrest symptoms and/or complications from the disease or infection. An amount adequate to accomplish this is defined as a "therapeutically effective dose."

The dose will be determined by the activity of the composition produced and the condition of the patient, as well as the body weight or surface areas of the patient to be treated. The size of the dose also will be determined by the existence, nature, and extent of any adverse side effects that accompany the administration of a particular composition in a particular patient. In determining the effective amount of the composition to be administered in the treatment or prophylaxis of diseases such as HSV infection, the physician needs to evaluate the production of an immune response against the virus, progression of the disease, and any treatment-related toxicity.

For example, a vaccine or other composition containing a subunit HSV protein can include 1–10,000 micrograms of HSV protein per dose. In a preferred embodiment, 10–1000 micrograms of HSV protein is included in each dose in a more preferred embodiment 10–100 micrograms of HSV protein dose. Preferably, a dosage is selected such that a single dose will suffice or, alternatively, several doses are administered over the course of several months. For compositions containing HSV polynucleotides or peptides, similar quantities are administered per dose.

In one embodiment, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an antiviral immune response, and is at least 10–50% above the basal (i.e., untreated) level. Such vaccines should also be capable of causing an immune response that leads to an improved clinical outcome in vaccinated patients as compared to non-vaccinated patients. In general, for pharmaceutical compositions and vaccines comprising one or more polypeptides, the amount of each polypeptide present in a dose ranges from about 0.1 μg to about 5 mg per kg of host. Preferably, the amount ranges from about 10 to about 1000 μg per dose. Suitable volumes for administration will vary with the size, age and immune status of the patient, but will typically range from about 0.1 mL to about 5 mL, with volumes less than about 1 mL being most common.

Compositions comprising immune cells are preferably prepared from immune cells obtained from the subject to whom the composition will be administered. Alternatively, the immune cells can be prepared from an HLA-compatible donor. The immune cells are obtained from the subject or donor using conventional techniques known in the art, exposed to APCs modified to present an epitope of the invention, expanded ex vivo, and administered to the subject. Protocols for ex vivo therapy are described in Rosenberg et al., 1990, New England J. Med. 9:570–578. In addition, compositions can comprise APCs modified to present an epitope of the invention.

Immune cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to enrich and rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., 1997, Immunological Reviews 157:177).

Administration by many of the routes of administration described herein or otherwise known in the art may be accomplished simply by direct administration using a needle, catheter or related device, at a single time point or at multiple time points.

In Vivo Testing of Identified Antigens

Conventional techniques can be used to confirm the in vivo efficacy of the identified HSV antigens. For example, one technique makes use of a mouse challenge model. Those skilled in the art, however, will appreciate that these methods are routine, and that other models can be used.

Once a compound or composition to be tested has been prepared, the mouse or other subject is immunized with a series of injections. For example up to 10 injections can be administered over the course of several months, typically with one to 4 weeks elapsing between doses. Following the last injection of the series, the subject is challenged with a dose of virus established to be a uniformly lethal dose. A control group receives placebo, while the experimental group is actively vaccinated. Alternatively, a study can be designed using sublethal doses. Optionally, a dose-response study can be included. The end points to be measured in this study include death and severe neurological impairment, as evidenced, for example, by spinal cord gait. Survivors can also be sacrificed for quantitative viral cultures of key organs including spinal cord, brain, and the site of injection. The quantity of virus present in ground up tissue samples can be measured. Compositions can also be tested in previously infected animals for reduction in recurrence to confirm efficacy as a therapeutic vaccine.

Efficacy can be determined by calculating the $IC_{50}$, which indicates the micrograms of vaccine per kilogram body weight required for protection of 50% of subjects from death. The $IC_{50}$ will depend on the challenge dose employed. In addition, one can calculate the $LD_{50}$, indicating how many infectious units are required to kill one half of the subjects receiving a particular dose of vaccine. Determination of the post mortem viral titer provides confirmation that viral replication was limited by the immune system.

A subsequent stage of testing would be a vaginal inoculation challenge. For acute protection studies, mice can be used. Because they can be studied for both acute protection and prevention of recurrence, guinea pigs provide a more physiologically relevant subject for extrapolation to humans. In this type of challenge, a non-lethal dose is administered, the guinea pig subjects develop lesions that heal and recur. Measures can include both acute disease amelioration and recurrence of lesions. The intervention with vaccine or other composition can be provided before or after the inoculation, depending on whether one wishes to study prevention versus therapy.

Methods

The invention provides a method for treatment and/or prevention of HSV infection in a subject. The method comprises administering to the subject a composition of the invention. The composition can be used as a therapeutic or prophylactic vaccine. In one embodiment, the HSV is HSV-2. Alternatively, the HSV is HSV-1. The invention additionally provides a method for inhibiting HSV replication, for killing HSV-infected cells, for increasing secretion of lymphokines having antiviral and/or immunomodulatory activity, and for enhancing production of herpes-specific antibodies. The method comprises contacting an HSV-infected cell with an immune cell directed against an antigen of the invention, for example, as described in the Examples presented herein. The contacting can be performed in vitro or in vivo. In a preferred embodiment, the immune cell is a T cell. T cells include CD4 and CD8 T cells. Compositions of the invention can also be used as a tolerizing agent against immunopathologic disease.

In addition, the invention provides a method of producing immune cells directed against HSV. The method comprises contacting an immune cell with an HSV polypeptide of the invention. The immune cell can be contacted with the polypeptide via an antigen-presenting cell, wherein the antigen-presenting cell is modified to present an antigen included in a polypeptide of the invention. Preferably, the antigen-presenting cell is a dendritic cell. The cell can be modified by, for example, peptide loading or genetic modification with a nucleic acid sequence encoding the polypeptide. In one embodiment, the immune cell is a T cell. T cells include CD4 and CD8 T cells. Also provided are immune cells produced by the method. The immune cells can be used to inhibit HSV replication, to kill HSV-infected cells, in vitro or in vivo, to increase secretion of lymphokines having antiviral and/or immunomodulatory activity, to enhance production of herpes-specific antibodies, or in the treatment or prevention of HSV infection in a subject.

The invention also provides a diagnostic assay. The diagnostic assay can be used to identify the immunological responsiveness of a patient suspected of having a herpetic infection and to predict responsiveness of a subject to a particular course of therapy. The assay comprises exposing T cells of a subject to an antigen of the invention, in the context of an appropriate APC, and testing for immunoreactivity by, for example, measuring IFNγ, proliferation or cytotoxicity. Suitable assays are described in more detail in the Examples.

EXAMPLES

The following examples are presented to illustrate the present invention and to assist one of ordinary skill in making and using the same. The examples are not intended in any way to otherwise limit the scope of the invention.

Example 1

Identification of Viral Epitopes in HSV-2 Tegument Proteins

This example shows the use of expression cloning with full-length viral DNA to identify T-cell antigens. Described herein are HSV epitopes recognized by lesion-infiltrating T-cells discovered by expression cloning. Details of the methods are described in U.S. Pat. No. 6,375,952, issued Apr. 23, 2002.

Lymphocyte Functional Assays

Triplicate proliferation assay wells contained $10^4$ cloned T-cells, $10^5$ irradiated (3300 rad) PBMC or $2.5 \times 10^4$ irradiated (8000 rad) EBV-LCL as antigen presenting cells (APC), and antigen in 200 µl T-cell media (D. M. Koelle et al., 1997, Human. Immunol., 53:195–205) in 96-well U-bottom plates. When heat-killed bacteria were used as antigen, the equivalent of $10^5$ cfu/well (prior to inactivation) was added and gentamicin (20 µg/ml) was included. After 72 hours, 1 µCi/well $^3$H thymidine was added for 18 hours, cells were harvested, and incorporation of thymidine evaluated by liquid scintillation counting. Standard deviations were less than 10% of the mean values. Results are reported as mean cpm or as delta cpm=mean cpm for experimental antigen minus mean cpm for control antigen. Control antigen was mock-infected cell lysate for whole viral antigens and pUEX2-derived β-galactosidase for recombinant protein preparations. To determine the reactivity of bulk-cultured lesion-derived T-cells, fusion proteins or control β-galactosidase were used at 10 µg/ml. To determine HLA restricting loci, HLA DR-specific mAb L243 (V. G. Preston et al., 1978, J. Virol., 28:499–517), HLA DP-specific mAb B7.21 (A. J. Watson et al., 1983, Nature, 304:358–360), or HLA DQ-specific mAb SpV-L3 (H. Spits et al., 1984, Eur. J. Immunol., 14:299–304) were used as described (D. M. Koelle et al., 1994, J. Virol. 68:2803–2810).

Cytolysis assays were performed in triplicate using 4-hour $^{51}$Cr release as described (D. M. Koelle et al., 1993, J. Clin. Invest., 91:961–968). Target EBV-LCL were infected for 18 hours with HSV-3 at a multiplicity of infection of 30 or pulsed with 1.0 µM peptide for 90 minutes prior to washing as described (W. W. Kwok et al., 1996, J. Exp. Med., 183:1253–1258). The effector to target ratio was 20:1. Spontaneous release was less than 28%.

Results

Fine Localization of T-Cell Epitopes

Figure 2:
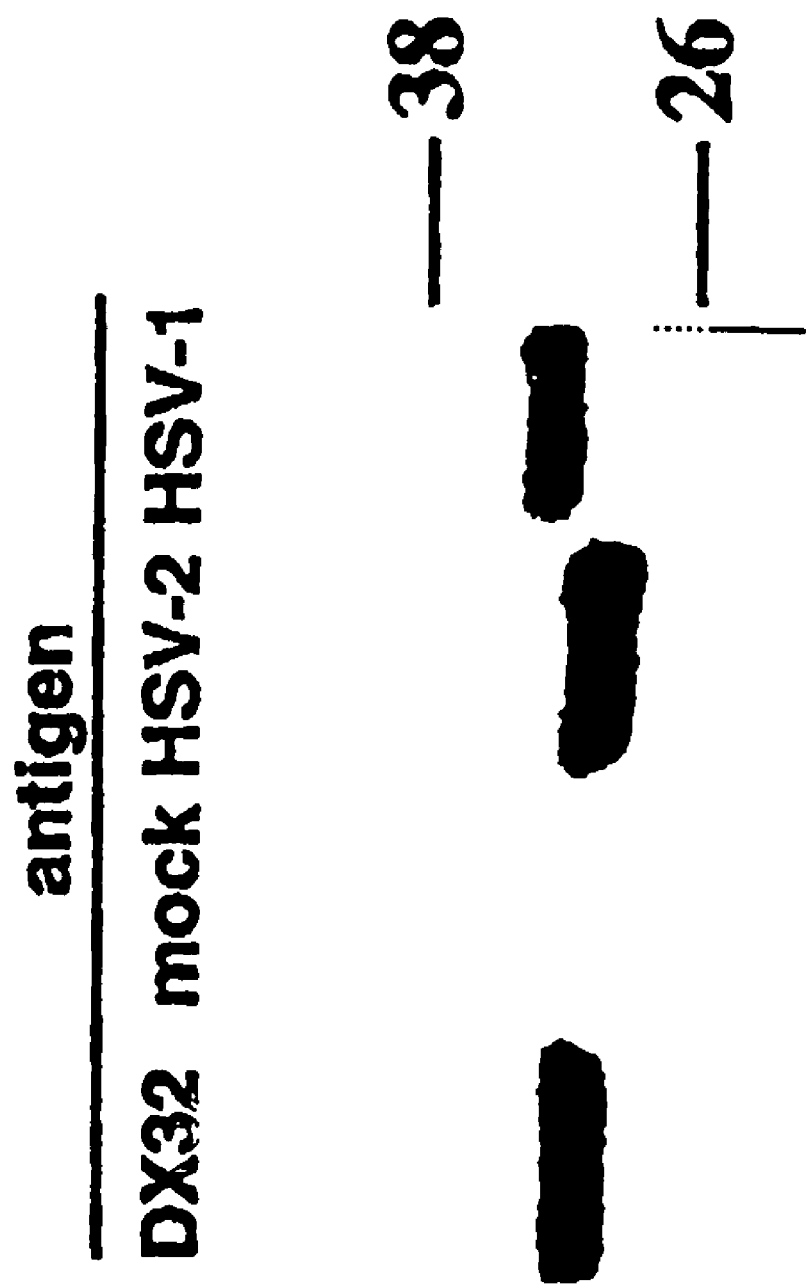
FIG. 2 is an immunoblot showing determination of the HSV viral phenotype of the $U_L49$ gene product (VP22) of IRV DX32. Lysates of mock-infected cells and cells infected with the viral strains DX32, HSV-1 or HSV-2 were separated by SDS-PAGE, blotted, and probed with VP22-specific mAb. The molecular weights (kD) of marker proteins are shown at right.

To reduce the complexity of libraries for expression cloning, TCC recognizing antigen(s) partially mapped using HSV-1×HSV-2 intertypic recombinant viruses (IRV) were selected. HSV DNA near 0.7 map unites encodes T-cell antigens in addition to VP16. Epitope mapping for TCC 4.2EI and 2.3 (D. M. Koelle et al., 1994, J. Virol., 68:2803–2810) was improved with IRV DX32 (FIG. 1A). This HSV-2 based virus contains a block of HSV-1 DNA near 0.7 map units (V. G. Preston et al., 1978, J. Virol., 28:499–517). The $U_L48$ gene product has the HSV-2 phenotype, as shown by reactivity with HSV-2 type-specific, VP16-specific (D. M. Koelle et al., 1994, J. Virol., 68:2803–2810) T-cell clone 1A.B.25. The $U_L49$ (FIG. 2) and $U_L50$ gene products (M. V. Williams, 1987, Virology, 156: 282–292; F. Wohlrab, 1982, J. Virol., 43:935–942) also have a HSV-2 phenotype. The HSV-2 DNA present in IRV DX32 therefore includes $U_L48$, $U_L49$, $U_L50$, and most likely the intervening $U_L49.5$. Since TCC 4.2E1 and 2.3 react with RS1G31 and DX32, but not with RP2 (FIG. 1B), recognition of $U_L49$, $U_L49.5$, or $U_L50$ is most likely.

Expression Cloning to Determine T-Cell Antigens

The BamH I w fragment of HSV-2 was selected for expression cloning, since it contains the $U_L49$, $U_L49.5$, and most of the $U_L50$ coding sequences (A. Cress and S. J. Triezenberg, 1991, Gene, 103:235–238; G. D. Elliott and D. M. Meredith, 1992, J. Gen. Virol., 73:723–736; N. J. Maidand et al., 1982, Infect. Immun., 38:834–842). 70–90% of random colonies contained an insert; all were of viral origin. The most active libraries (Table 1) for each TCC (pUEX1 for TCC 4.2E1, pUEX 3 for TCC 2.3) were selected and an individual reactive bacterial clone detected by sequential testing of pools and individual colonies (Table 2). Clone 1.1.3 encodes a fusion protein eliciting proliferation by TCC 4.2E1. This clone contains a backwards 80 bp Sma I fragment of $U_L49$, a 262 bp Sma I fragment of HSV-2 $U_L49$ DNA predicted to encode amino acids 105 to 190, forward and in-frame with regards to β-galactosidase, and a 246 bp Sma I fragment of $U_L49$ forward but out of frame due to a deletion of a single C residue at the 262 bp Sma I fragment-242 bp Sma I fragment junction. Clone 3.19 contained a 583 bp Sma I fragment encoding amino acids 118–312 of $U_L50$, followed by backwards 80 and 96 bp Sma I fragments of $U_L49$.

TABLE 1

Identification of protein libraries eliciting proliferation (mean cpm [$^3$H]thymidine incorporation) of HSV-specific TCC. Autologous EBV-LCL (clones 4.2E1 and 2.3) or PBMC were used as APC and library-derived fusion protein antigens were diluted 1:300. Data are mean cpm [$^3$H] thymidine incorporation.

| | library[1] | | | control stimuli[2] | |
|---|---|---|---|---|---|
| TCC | pUEX1-BamH I "w"-Sma I | pUEX2-BamH I "w"-Sma I | pUEX3-BamH I "w"-Sma I | media | HSV-2 |
| 4.2E1 | 10,105 | 4,150 | 1,903 | 286 | 21,591 |
| 2.3 | 418 | 785 | 2,279 | 102 | 11,014 |
| | pUEX1-HG52-Sma I-Alu I | pUEX2-HG52-Sma I-Alu I | pUEX3-HG52-Sma I-Alu I | | |
| ESL4.9 | −52 | −25 | 16,235 | 146 | 66,013 |
| ESL2.20 | 1 | 768 | 5,427 | 123 | 13,359 |

[1]Library names list expression vector, name of HSV-2 restriction fragment or strain of full-length viral DNA, and restriction enzyme(s) used to digest viral DNA.
[2]10$^5$ autologous irradiated (3300 rad) PBMC and either mock-infected cell lysate or UV-treated HSV-2 antigen.

Figure 3:
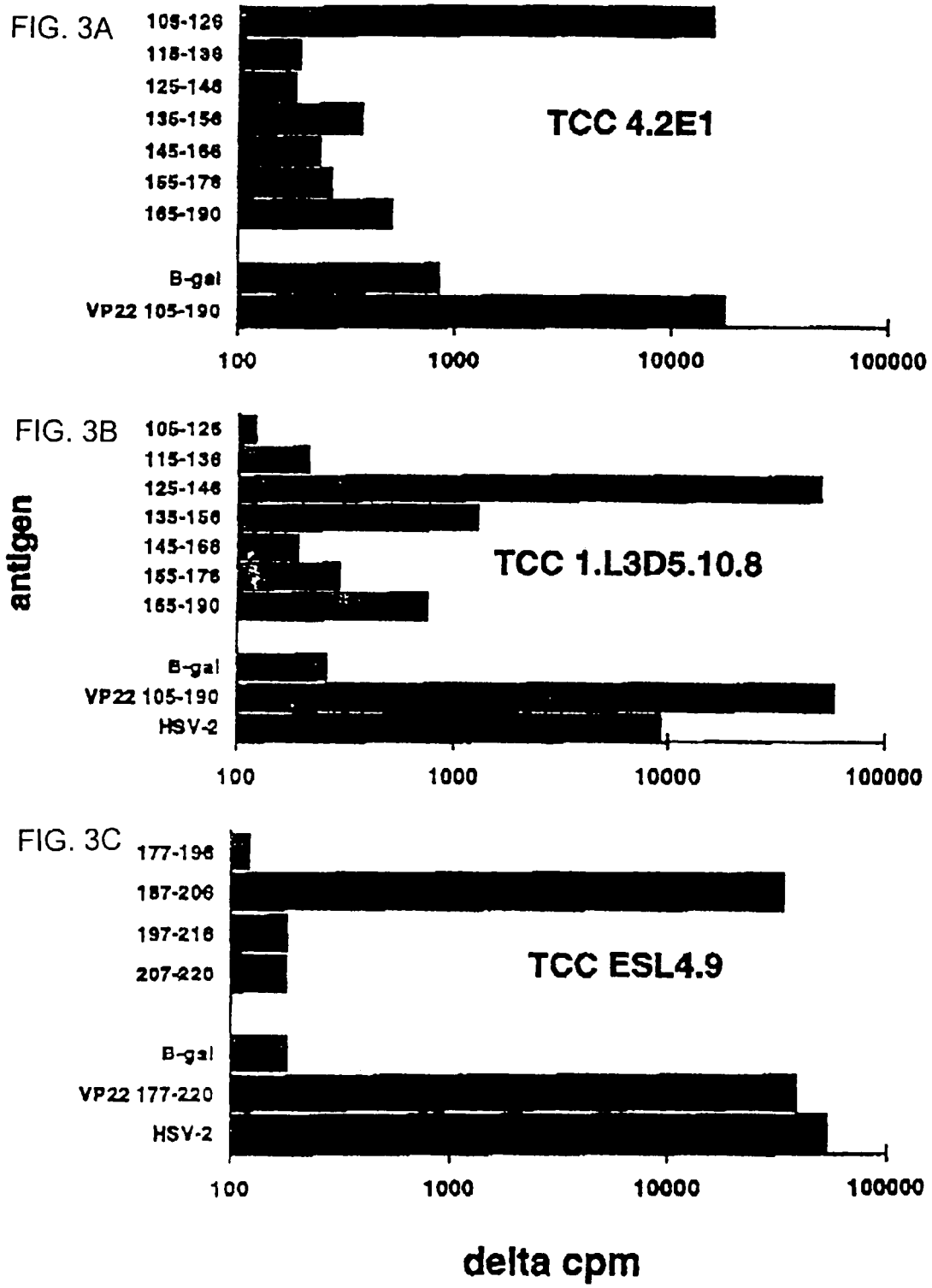
FIG. 3A is a bar graph showing T-cell proliferation elicited by various peptide epitopes in VP22 of HSV-2 using TCC 4.2E1. Antigen-presenting cells (APC) were autologous EBV-LCL. Antigens included β-galactosidase and fusion proteins used at 10 µg/ml and peptides used at 3 µM. Data are delta cpm [$^3$H] thymidine incorporation compared to media alone, which was less than 500 cpm in each case.
FIG. 3B is a bar graph showing T-cell proliferation elicited by various peptide epitopes in VP22 of HSV-2 using TCC 1.L3D5.10.8. APC were autologous PBMC. Antigens included β-galactosidase and fusion proteins used at 10 µg/ml and peptides used at 1 µM. Data are delta cpm [$^3$H] thymidine incorporation compared to media alone, which was less than 500 cpm in each case.
FIG. 3C is a bar graph showing T-cell proliferation elicited by various peptide epitopes in VP22 of HSV-2 using TCC ESL4.9. APC were autologous PBMC. Antigens included β-galactosidase and fusion proteins used at 10 µg/ml and peptides used at 1 µM. Data are delta cpm [$^3$H] thymidine incorporation compared to media alone, which was less than 500 cpm in each case.
Figure 4:
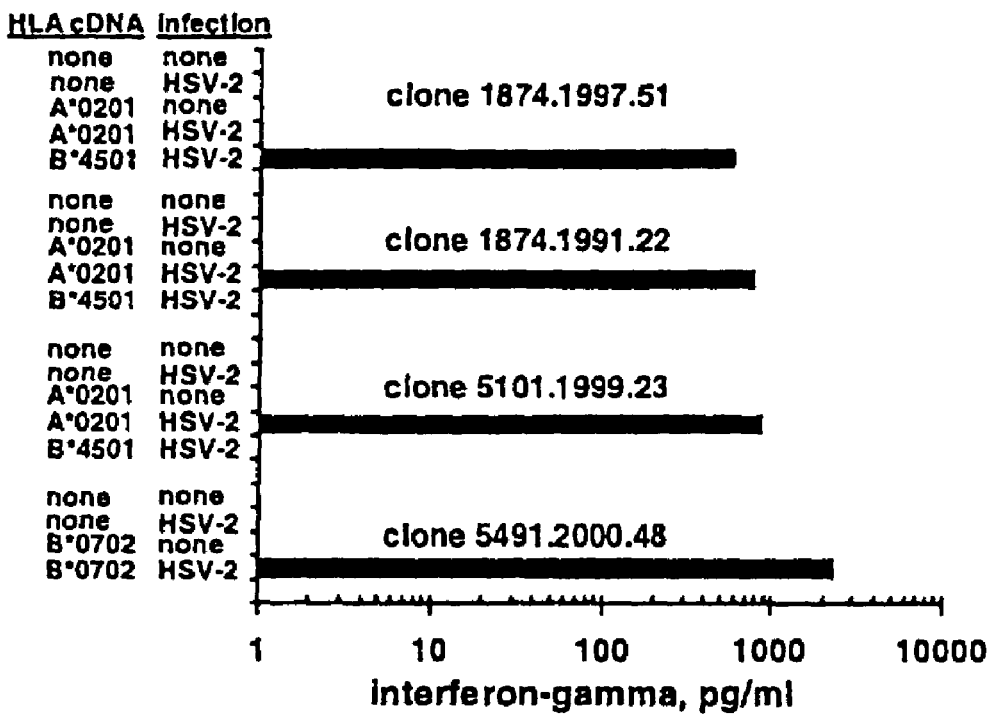
FIG. 4 shows secretion of IFN-γ by lesion-derived CD8$^+$ T cell clones in response to COS-7 cells transfected with HLA class I heavy chain cDNA and infection with HSV-2 strain 333. Values are mean of duplicate IFN-γ secretion into medium, measured by ELISA.

Identification of T-cell antigens was confirmed by targeted subcloning and overlapping peptides. The 262 bp Sma I fragment of $U_L49$ of HSV-2 encoding amino acids 105–190 was subcloned into pUEX3 to yield plasmid 49.262.12. This protein stimulated TCC 4.2E1 (Table 2). Only peptide 105–126 of VP22 of HSV-2 (GGPVGAGGRSHAPPARTP-KMTR; SEQ ID NO: 4) was stimulatory (FIG. 3). DNA fragments encoding $U_L50$ 118–312 and 118–250 were subcloned into pUEX3. Fusion proteins expressing these fragments were active (Table 2).

lymphoproliferation assays at the pool (5–12 bacterial clones) and final assay stages.

Sequencing of plasmids in positive bacteria showed that TCC ESL4.9 recognized a 44 amino acid fragment of $U_L49$ gene product VP22 (amino acids 177–220), while TCC ESL2.20 recognized a 34 amino acid fragment of $U_L21$ (amino acids 148–181) (Table 2). In both cases single Alu I fragments of HSV-2 DNA were inserted in-frame and forwards. Peptide mapping revealed that amino acids 187–206 (FIG. 3C) stimulated TCC ESL4.9.

TABLE 2

Antigenic specificity of HSV-2 reactive TCC. Bacterially-derived recombinant fusion protein antigens were used at 1:900 dilution. Autologous EBV-LCL (clone 4.2E1) or PBMC were used as APC. Data are delta cpm [$^3$H] thymidine incorporation compared to media, which was less than 500 cpm in each case.

| | recombinant antigen | | | control antigens | | |
|---|---|---|---|---|---|---|
| TCC | Clone name | viral sequence[1] | cpm | pUEX2 β-gal | HSV-1 | HSV-2 |
| 4.2E1 | 1.1.3 | VP22 105–190 | 4,875 | 93 | nd | nd |
| | 49.262.12[2] | VP22 105–190 | 6,898 | | | |
| 2.3 | 3.19 | $U_L50$ 118–312 | 43,971 | 231 | 543 | 53,032 |
| | 50.583.44[3] | $U_L50$ 118–312 | 34,453 | | | |
| | 50.397[3] | $U_L50$ 118–250 | 66,501 | | | |
| ESL4.9 | C11 | VP22 177–220 | 59,400 | 166 | 112,803 | 64,685 |

[1]Amino acids predicted forward and in-frame with β-galactosidase from sequence data.
[2]Confirmatory subclone of 1.1.3 containing only a 262 bp Sma I fragment of $U_L49$ DNA forward and in-frame with pUEX3.
[3]Confirmatory subclones of 3.19 containing a 583 bp Sma I fragment of $U_L50$ or a 397 bp Sma I-Stu I fragment of $U_L50$ DNA forward and in-frame with pUEX3.

Evaluation of random colonies from full-length HSV-2 DNA libraries showed that 80–100% contained plasmids with an insert; 80–100% of inserts were of viral origin. For both TCC ESL4.9 and ESL2.20, only the pUEX3 protein library elicited lymphoproliferation (Table 1). Since the libraries were more complex than for those made from the BamH I w fragment, 2,000–3,000 bacterial transformants were screened by a combinatorial method. In preliminary experiments, heat-killed, washed bacteria were found to substitute for inclusion body preparations of protein in Fusion Proteins as Probes of Bulk Lesion-Infiltrating T-Cells Newly discovered T-cell antigens were added to the panel of HSV antigens used to probe bulk cultures of lesion-infiltrating T-cells. The first available specimens were a set of four biopsies (2 mm each) obtained from day 5 (virus culture positive) of a buttock recurrence of HSV-2 from patient 1 (D. M. Koelle et al., 1998, J. Clin. Invest. 101: 1500–09; D. M. Koelle et al., 1994, J. Virol., 68:2803–2810). All four biopsies showed reactivity with VP22 105–190 but not β-galactosidase, glycoproteins B or D, or VP16. TCC were derived after restimulating the original bulk culture for one cycle with VP22 105–190 fusion protein. Proliferative responses of TCC 1.L3D5.10.8 (FIG. 3B) to VP22 (105–190) and constituent peptides document a third T-cell epitope in VP22 contained within amino acids 125–146.

HLA Restriction

The HLA restriction of the TCC recognizing antigens encoded near 0.7 map units was determined in detail. Proliferation of TCC 4.2E1, specific for VP22 105–126, is inhibited 84% by anti-DP, but less than 20% by anti-DR or anti-DQ mAb. TCC 4.2E1 is from a DPB1*2001/DPB1*0402 heterozygous donor. Allogeneic EBV-LCL bearing DPB1*2001, but not DPB1*0402, present antigen (Table 3), establishing restriction by DPB1*2001. Proliferation of TCC 2.3, specific for $U_L 50$, was inhibited by anti-DR but not anti-DP or anti-DQ mAb. This clone is from a DRB1*0301/BRB1*0701 heterozygous donor. Allogeneic PBMC from a DRB1*0301 donor presented antigen, consistent with binding of antigenic peptide to this allele. However, presentation by the linked DR gene products DRw52 or DRw53, cannot be ruled out. Additional HLA restriction studies are summarized in Table 4.

TABLE 3

Determination of restricting HLA allele of lesion-derived CD4 TCC 4.2E1 and 2.3. Antigens were β-gal fusion proteins (Table 2) at 1:900 dilution. Data are delta cpm [$^3$H] thymidine incorporation compared to media, which was less than 500 cpm in each case.

| T-cell clone | antigen | APC | HLA type[1] | delta cpm[2] |
|---|---|---|---|---|
| 4.2E1 | 1.1.3 | autologous EBV-LCL | DPB1*0402, 2001 | 30,719 |
|  |  | AMAI EBV-LCL | DPB1*0402 | 2,732 |
|  |  | ARENT EBV-LCL | DPB1*2001 | 26,218 |
| 2.3 | 50.583.44 | autologous PBMC | DRB1*0301, 0701 | 8,964 |
|  |  | allogeneic PBMC A | DRB1*0701, 1001 | 45 |
|  |  | allogeneic PBMC B | DRB1*0301, 1301 | 19,223 |

[1]HLA type at the HLA class II locus as determined by inhibition with mAb.
[2]In comparison to pUEX2 control protein (1:1000 dilution) with the same APC, which caused less than 500 cpm [$^3$H]thymidine incorporation in each case.

The HLA restriction of TCC BM.17 was studied in detail. Proliferation of TCC BM.17 and the similar clone SB.17 was inhibited 90% by anti-DQ, but less than 25% by Anti-DR or anti-DP mAb. Donors BM and SB are heterozygous for HLA DQB1*0201/0501. At high concentrations of peptide, both DQB1*0201- and DQB1*0501 homozygous EBV-LCL appeared to present antigen to TCC BM.17.

CTL Activity of Tegument-Specific CD4 T-Cell Clones

Cytotoxic activities of the CD4 TCC with newly and previously identified specificities were tested using EBV-LCL target cells (Table 4). All clones tested displayed cytolytic activity towards peptide-loaded target cells. Cytolytic activity against target cells infected with HSV-2 showed greater variability. VP22-specific TCC 4.2E1 was active, while VP22-specific TCC from other donors were not.

Discussion

HSV-specific T-cells selectively infiltrate recurrent genital HSV-2 lesions (D. M. Koelle et al., 1994, J. Infect. Dis., 169:956–961). Local CTL activity, with CD4 and CD8-mediated components, is correlated with viral clearance (D. M. Koelle et al., 1998, J. Clin. Invest. 101:1500–09). The antigens recognized by local HSV-specific T cells are diverse and in many cases unknown (D. M. Koelle et al., 1994, J. Virol., 68:2803–2810). This example documents recognition of tegument protein VP22.

The expression cloning system described herein works well with HSV. Genomic double stranded DNA can be used directly since introns are rare in the HSV genome. The same HSV-2 strain, HG52 (A. Dolan et al., 1998, J. Virol. 72:2010–2021) was used to screen candidate lesion-derived TCC and make protein libraries. The relatively low degree of strain variability (M. J. Novotny et al., 1996, Virology, 221:1–13) between HSV-2 strains in the donors and HG52 might rarely lead to omission of epitope(s) recognized in vivo; application to viruses with more strain variation would benefit from the use of autologous isolates.

Notably, reactivity with VP22 was detected in two independent expression cloning experiments with lesion-infiltrating TCC from two donors. VP22 reactivity was also detected during screening of the first available set of bulk lesion-infiltrating lymphocyte cultures. Ten additional

TABLE 4

Cytolytic activity of lesion-derived, tegument-specific CD4 TCC with summary of fine specificity and HLA restriction. Results are percent specific release at an effector to target ratio of 20:1 except ESL4.34 (10:1). Auto = autologous EBV-LCL as target cells; allo = allogeneic EBV-LCL mismatched at the relevant HLA locus (if known) or mismatch at HLA DR and DQ.

|  |  |  | cytolysis assay target | | | | | |
|---|---|---|---|---|---|---|---|---|
| TCC | specificity[1] | HLA restriction[2] | auto HSV-2 | auto peptide | auto mock | allo HSV-2 | allo peptide | allo mock |
| 4.2E1 | VP22 105–126 | DPB1*2001 | 20.7 | 44.2 | −4.1 | −2.9 | −1.7 | 4.6 |
| ESL4.9 | VP22 187–206 | DR[3] | −0.6 | 20.2 | 1.3 | 0 | 0 | 0 |
| 1.L3D5.10.8 | VP22 125–146 | DR[4] | 1.1 | 61.1 | −0.3 | −0.4 | −0.6 | −0.4 |
| 1.L3D5.10.12 | VP22 125–146 | DR[4] | 2.5 | 57.6 | 1.6 | −0.1 | −2.5 | −1.4 | na = not available since epitope mapping was not done and synthetic antigenic peptide was not made.
nd = not done.
[1]Indicates peptide used (1 μM) to load targets in CTL assay for selected TCC.
[2]Maximum extent of definition of HLA restricting locus and/or allele. Subjects RH and KM were typed serologically; others were typed at the DNA level.
[3]Subject is heterozygous for HLA DRB1*0402 and DRB1*1301 and restricting allele has not been determined.
[4]Subject is heterozygous for HLA DRB1*0301 and DRB1*1102 and restricting allele has not been determined.

clones from three patients have been negative with the disclosed fragments of $U_L49$, $U_L21$, and $U_L50$.

Tegument antigens may be suitable targets for lesion-infiltrating CD4 T-cells because of their abundance. VP16 and VP22 are present in large amounts: on the order of $1.6 \times 10^3$ molecules of VP16 (Y. Zhang and J. L. C. McKnight, 1993, J. Virol., 67:1482–1492) and $2.5-2.8 \times 10^3$ molecules of VP22 (J. Leslie et al., 1996, Virology, 220:60–68) are incorporated into each virion in HSV-1.

Because polypeptides expressed as C-terminal fusion to VP22 can be co-transported into cells, expression of proteins as VP22 fusions may be of interest as a type of adjuvant preparation. This can be tested by expression of heterologous epitopes in VP22. VP16 and VP22 of HSV-1 are strongly, noncovalently associated in infected cells as shown by coimmunoprecipitation. These proteins co-localize in the perinuclear area of cells (G. Elliott et al., 1995, J. Virol., 69:7932–7941; G. D. Elliott et al., 1992, J. Gen. Virol., 73:723–736).

In summary, expression cloning has allowed discovery of novel HSV T-cell antigens. The in situ enrichment of antigen-specific CD4 T-cells in lesions allows study of the antigenic repertoire unbiased by secondary in vitro stimulation with antigen. The favorable characteristics of the HSV genome allow direct use of libraries of whole viral DNA. Tegument proteins are candidates together with membrane glycoproteins for use as HSV vaccines in humans.

Example 2

Efficacy of Full-Length $U_L49$

This Example shows that the full-length $U_L49$ protein is effective at stimulating T cell proliferation. The data demonstrate the antigenicity of full-length $U_L49$ expressed in *E. coli* and in Cos-7 cells. These results confirm that the antigens described hereinabove were accurately identified.

To express full-length $U_L49$ protein of HSV-2 in a prokaryotic system, the gene was cloned by PCR from DNA prepared from HSV type 2 strain HG52 using primers GGAAGATCTACCTCTCGCCGCTCCGTCA (SEQ ID NO: 5) at the 5' end of the gene and CCGGAATTCTTGTCTGTCGTCTGAACGCG (SEQ ID NO: 6) at the 3' end of the gene. PCR product was digested with Bgl II and EcoR I and cloned into the Bgl II and EcoR I sites in the TA cloning vector pcR2.1-Topo (Invitrogen). The gene was then subcloned into the vector pTrcHisB (Invitrogen) and then into pGEX-2T (Pharmacia). The sequence of the HSV-2 $U_L49$ clone had one coding mutation compared to the published sequence (Dolan 1998): amino acid 244 was mutated from serine to proline. The predicted amino acid sequence of the expressed protein also is missing the initial methionine. $U_L49$ contains an N-terminal fusion domain derived from vector pGEX2T. This plasmid is named pGEX2T-UL49HSV2.

To make prokaryotically expressed full length $U_L49$ of HSV-2, pGEX2TU-L49HSV2 or control empty vector was transformed into *E. coli* strain BL21 Bacteria in log-phase growth were adjusted to an $OD_{600}$ of 0.4 in LB-ampicillin media. To some tubes isopropyl beta-D-thiogalactopyranoside (IPTG) was added to 0.3 mM. Bacteria were cultured for 1.5 hours at 37° C. with rotation. Bacteria were collected by centrifugation and washed 3× in PBS containing 1 mM EDTA, heated to 65° C. for 10 minutes, and washed twice more with PBS, and resuspended at approximately $1 \times 10^9$ bacteria/ml in T-cell medium. Heat-killed bacterial suspensions were used as test antigen.

To express full-length $U_L49$ protein of HSV-2 in a eukaryotic system, the gene was separately re-amplified by polymerase chain reaction using a high-fidelity DNA polymerase with proof-reading function. The same primers and template were used. The gene was cloned directly into the Bgl II and EcoR I sites of pEGFP-C1 (Clontech). The entire $U_L49$ gene was sequenced and agreed with published sequence. The predicted amino acid sequence of the expressed protein is identical to that predicted for viral $U_L49$ except that the initial methionine at amino acid 1 is missing. A N-terminal fusion domain derived from vector pEGFP-C1 is also predicted to be expressed. This plasmid is named pEGFP-C1-UL49HSV2.

To make eukaryotically expressed full length $U_L49$ of HSV-2, pEGFP-C1-UL49HSV2 plasmid DNA or pEGFP-C1vector control DNA was transfected into Cos-7 cells by lipofection. After 48 hours, cells were scraped and sonicated and a supernatant and pellet phase prepared. Cells from a 9.4 cm$^2$ dish were used to prepare 300 microliters of supernatant. The pellet from a 9.4 cm$^2$ dish was resuspended in 300 microliters medium. Supernatant and pellet preparations were used as test antigens.

These test antigens were added to assay wells (96-well, U-bottom) in 200 microliters of T-cell medium containing $1 \times 10^5$ autologous irradiated peripheral blood mononuclear cells (PBMC) per well and $1 \times 10^4$ lesion-derived CD4-bearing T-cell clone ESL4.9 for $U_L49$ (Koelle et al, 1994 and 1998). Assays were performed in duplicate or triplicate. After three days, $^3H$ thymidine incorporation was measured as described in Example 1.

Results are expressed as stimulation index (mean cpm $^3H$ thymidine incorporation test antigen/mean cpm $^3H$ thymidine incorporation media control) and delta cpm (mean cpm $^3H$ thymidine incorporation test antigen minus mean cpm $^3H$ thymidine incorporation media control). Positive and negative control antigens were run as indicated and as described in Example 1.

TABLE 5

Antigenicity of full-length HSV-2 $U_L$ 49 expressed prokaryotically in *E. coli* BL21

| antigen | final dilution | delta cpm | stimulation index |
| --- | --- | --- | --- |
| UV HSV-2 | 1:100 | 26,823 | 386 |
| heat-killed pGEX2 | 1:4 | −11 | 0.84 |
| heat-killed pGEX2 | 1:40 | −25 | 0.64 |
| heat-killed pGEX2 | 1:400 | −8 | 0.89 |
| heat-killed pGEX2-UL49HSV2 | 1:4 | 9,413 | 135 |
| heat-killed pGEX2-UL49HSV2 | 1:40 | 10,526 | 152 |
| heat-killed pGEX2-UL49HSV2 | 1:400 | 5,021 | 73 |

TABLE 6

Antigenicity of full-length HSV-2 $U_L$ 49 expressed eukaryotically in Cos-7 cells

| antigen | final dilution | delta CPM | stimulation index |
| --- | --- | --- | --- |
| UV-mock virus | 1:100 | −4 | 0.96 |
| UV HSV-2 | 1:100 | 46,510 | 470 |
| supernatant of control-transfected cells | 1:4 | 8 | 1.08 |

TABLE 6-continued

Antigenicity of full-length HSV-2 $U_L$ 49 expressed eukaryotically in Cos-7 cells

| antigen | final dilution | delta CPM | stimulation index |
|---|---|---|---|
| pellet of control-transfected cells | 1:4 | 131 | 2.32 |
| supernatant of $U_L$ 49-transfected cells | 1:4 | 1,512 | 16.3 |
| pellet of $U_L$ 49-transfected cells | 1:4 | 84,951 | 859 |
| pellet of $U_L$ 49-transfected cells | 1:40 | 35,753 | 362 |
| pellet of $U_L$ 49-transfected cells | 1:400 | 29,854 | 302 |

These results show that HSV-2 protein $U_L$49 retains its immunogenicity when expressed as a full-length protein. $U_L$49 was studied in both prokaryotic and eukaryotic systems.

Example 3

Prevalence of Antigens in Population

This example supports the utility of preventative and therapeutic uses of the antigens of the invention by demonstrating the prevalence of responses to these antigens among the population. To do this, seven individuals who were HSV-2 infected as documented by type-specific serology were surveyed. These individuals were different from the individuals from whom the index T-cell clones were recovered from HSV-2 lesions.

For each subject, PBMC were isolated and plated at $2 \times 10^6$ cells/well in 2 mls of T-cell medium in 24-well plates and stimulated in vitro with a 1:500 dilution of UV-inactivated HSV-2 strain 333 for five days. At that time, 40 units/ml recombinant human IL-2 was added for an additional five to six days, giving rise to a short-term, HSV-specific cell line termed a B1 cell line.

Reactivity to individual HSV-2 proteins was assessed as follows. Proliferation assays were set up on 96-well round bottom microtiter plates, and each condition was performed in triplicate. To each well, $1 \times 10^5$ autologous irradiated (3300 rad gamma) PBMC were added as antigen presenting cells. To each well, $1 \times 10^4$ B1 cells were added. The following control substances were added: media, UV-treated mock virus preparation diluted 1:500, UV-treated HSV-2 strain 333 diluted 1:500, glycoproteins B or D or VP16 protein of HSV-2 (purified) at 4 micrograms per ml final concentration. The response to UV-treated HSV-2 was expected to be positive and served as a positive control for the viability and overall specificity of the cells. Glycoproteins B and D and VP16 were previously shown to be targets of HSV-specific T-cells (D. M. Koelle et al., 1994, J. Virol 68(5):2803–2810).

For the newly discovered antigen UL49, the cloning of the full-length gene and its expression in the eukaryotic Cos-7 system was as described above, as was the preparation of control antigens based on the empty vector. The supernatant and pellet after sonication of transfected Cos-7 cells was used at a final dilution of 1:20 in triplicate proliferation assays.

Positive responses were scored if the stimulation index (mean cpm $^3$H thymidine incorporation for test antigen/mean cpm $^3$H thymidine incorporation for relevant control antigen) was greater than or equal to 4.0. For UV HSV-2 antigen, the relevant control antigen was UV-mock virus. For gB2, gD2, and VP16, the control was media. For the new antigens expressed in Cos-7 cells, the control antigen was either the pellet or supernatant of Cos-7 cells transfected with control empty vector. Results are shown in Table 7. Reactivity with each of the newly discovered antigens was documented in at least one study subject. Overall, reactivity with $U_L$ 49 was observed more frequently and similar to that for the known antigens gB2 and gD2. These data provide support that human individuals, in addition to the index subjects in whom the T-cell reactivity was originally described, are capable of reacting to these antigenic HSV-derived proteins.

TABLE 7

Antigenicity of known and of newly discovered HSV-2 antigens among a group of seven randomly chosen HSV-2 infected immunocompetent adults.

| | ANTIGEN | | | | |
|---|---|---|---|---|---|
| | HSV-2 | gB2 | gD2 | VP16 of HSV-2 | $U_L$ 49 of HSV-2 |
| n | 7 | 5 | 5 | 0 | 5 |
| % | 100 | 71 | 71 | 0 | 71 |

Example 4

Detection of HSV-Specific CD8 CTL in Recurrent Genital HSV-2 Lesions

This example demonstrates that specific CD8 CTL localize to genital HSV-2 lesions. This is shown by serial lesion biopsy studies of recurrent genital HSV-2 lesions using cells that have encountered antigen/APC in situ and are not restimulated with antigen in vitro prior to readout assays.

To study the cDNA species derived from the positive genomic clone containing portions of ICP0 (Results), COS-7 cells (100 mm$^2$) were transfected with the ICP0 genomic clone, and total RNA was prepared after 48 h. The primer used for cDNA synthesis (TGC<u>TCTAGA</u>GACTC GATCCCTGCGCGTCGG; XbaI site underlined) (SEQ ID NO: 7) was from the 3'-end of the HSV-2 DNA in the ICP0 genomic clone. Moloney murine leukemia virus reverse transcriptase (Life Technologies) was used per the manufacturer. To examine splicing, PCR used pfu cDNA polymerase, the above 3'-primer, and 5'-primer TAA <u>GGTACC</u>TGAACCCCGGCCCGGCACGAGC (SEQ ID NO: 8) (KpnI site). To isolate exon 1 (Dolan, A. et al., 1998, J. Virol. 72:2010) of ICP0, PCR used the same 5'-primer and 3'-primer TGC<u>TCTAGA</u>CCAGGCGTGCGGGGCGGCG GG (SEQ ID NO: 9) (XbaI site). Reaction conditions were individually optimized. Product was digested with Acc65I and XbaI, gel purified, and ligated into similarly treated pCDNA 3.1-His-B, and in-frame insertion was confirmed by sequencing.

Full-length $U_L$ 47 of HSV-2 was cloned by PCR into pCDNA3.1/His-C using 5'-primer CTA<u>GGATCC</u>CTC CGGCCACCATGTCC (SEQ ID NO: 10) and 3'-primer CGA<u>TCTAGA</u>CCTATGGGCGTGGCGGGC (SEQ ID NO: 11) (BamHI and XbaI sites underlined). Full-length $U_L$ 46 of HSV-2 was cloned by PCR into pCDNA3.1/His-C with 5'-primer CGA<u>GGATCC</u>GTCTCCGCCATGCAACGCCG (SEQ ID NO: 12) and 3'-primer CGC<u>TCTAGA</u>TTTAATG GCTCTGGTGTCG (SEQ ID NO: 13) (BamHI and XbaI sites underlined). Similarly, a construct expressing aa 1–590 of $U_L$ 47 was made by PCR, using the above 5'-primer, an appropriate 3'-primer, and pcDNA3.1/His-C. Expression of aa 1–535 and 536–696 of $U_L$ 47 was driven by constructs derived from fill-length $U_L$ 47 using a naturally occurring NotI site at aa 535. In-frame vector-HSV-2 fusion at the 5'-end of the HSV-2 DNA was confirmed by sequencing in each case.

Results

TABLE 8

CTL activity and HLA restriction of CD8 clones, and initial results of expression cloning[1]

|  | CD8 CTL Clone | | |
| --- | --- | --- | --- |
|  | 1874.1991.22 | 5101.1999.23 | 5491.2000.48 |
| Autologous targets | | | |
| Mock | 1.2 | 6 | 1.2 |
| HSV-1 | 0.1 | 0 | 2.3 |
| HSV-2 | 38.3 | 56.6 | 63.2 |
| HSV-2 hr 259 (ICP4−) | 21.3 | 41.0 | ND |
| HSV-2/actinomycin D | 45.1 | 35.8 | 49.2 |
| HLA-mismatched targets | | | |
| Mock | 0 | 2.5 | 9.8 |
| HSV-2 | 0 | 2.1 | 7.0 |
| HLA restriction testing | | | |
| Matched allele | A*0201 | A*0201 | B*0702 |
| Mock | 3.3 | 0 | 5.1 |
| HSV-2 | 65.2 | 33.4 | 69.1 |
| Specificity | | | |
| Positive genomic clone | C:1:F1:C7 | C:2:C10:B9 | UL49-pEGFP-C1 |
| Nucleotides | 102,875–101,383 | 102,943–102,876 | 107,149–106,247 |
| Predicted HSV-2 ORF(s) | $U_L$ 47 300–696 . . . $U_L$ 46 1–71 | $U_L$ 47 278–298 | UL 49 1–300 |

[1]Data are percent specific release in $^{51}$Cr release assays at E:T 20:1. For actinomycin D experiments, target cells infected with wild-type HSV-2 were assayed in the presence of 5 µg/ml actinomycin D from 0.5 h before infection through the assay. To assess HLA restriction, allogeneic EBV-LCL were either mismatched at HLA-A and -B or matched with the index subject at only the indicated HLA class I allele. The positive HSV-2 genomicclones are listed by indicating the positive pCDNA3.1/His A, B, or C library: positive library plate: positive library well: positive final well. For 5491.2000.48, full-length $U_L$ 49 of HSV-2 in pEGFP-C1 (Clontech) was positive. The nucleotide numbers and predicted amino acid numbers within the antigenic HSV-2 DNA fragments are given as reported for the HSV-2 strain HG52 genomic sequence (28).

Recognition of Tegument HSV-2 Ags by CD8 T Cells

CD8 clone 5101.1999.23 recognized COS-7 cells co-transfected with HLA A*0201 and a HSV-2 Sau3aI fragment from bp 102,943–102,876 (Dolan, A. et al., 1998, J. Virol. 72:2010) (Table 8). The predicted fusion protein contains HSV-2 $U_L$ 47 aa 278–298. Reactivity with $U_L$ 47 was confirmed by cotransfection of A*0201 and full-length HSV-2 $U_L$ 47 (Table 9).

TABLE 9

Confirmation and localization of epitopes recognized by CD8+ clones[1]

| T Cell Clone | HSV-2 ORF and Predicted Amino Acids | HLA cDNA | IFN-γ (pg/ml) |
| --- | --- | --- | --- |
| 5101.1999.23 | None | None | 0 |
|  | $U_L$47 aa 1–696 (full length) | None | 0 |
|  | None | A*0201 | 0 |
|  | $U_L$47 aa 1–696 | A*0201 | >3000 |
| 1874.1991.22 | None | None | 0 |
|  | $U_L$47 aa 1–696 | None | 0 |
|  | None | A*0201 | 0 |
|  | $U_L$46 aa 1–722 (full length) | A*0201 | 0 |
|  | $U_L$47 aa 1–696 | A*0201 | 2984 |
|  | $U_L$47 aa 1–535 | A*0201 | 0 |
|  | $U_L$47 aa 1–590 | A*0201 | >3000 |
|  | $U_L$47 aa 536–696 | A*0201 | >3000 |
| 1874.1997.51 | Genomic, nucleotides 1858–3022 | None | 0 |
|  | None | B*4501 | 0 |
|  | Genomic, nucleotides 1858–3022 | B*4501 | >600 |
|  | ICP0 exon 1 cDNA aa 1–25 | B*4501 | 3.2 |
|  | ICP0 exon 1/start of exon 2 cDNA aa 1–105 | B*4501 | >600 |

[1]The indicated CD8 CTL clones were reactive with HSV-2 genomic clones indicated in Table 8. COS-7 cells were transfected with HLA cDNA and HSV-2 DNA or cDNA as shown. T cell activation was detected by IFN-γ secretion, reported as the mean of duplicate wells. Two CTL clones are shown to react with $U_L$47. The epitope recognized by clone 1874.1991.22 is localized to aa 535–590 of $U_L$47, and the epitope recognized by clone1874.1997.51 is localized to aa 26–105 of ICP0. Values are mean of duplicate IFN-γ secretion into the medium as measured by ELISA. ORF, Open reading frame.

The CD8 T cell clone 1874.1991.22 recognized COS-7 cells cotransfected with HLA A*0201 and a HSV-2 Sau3aI fragment from bp 102,875–101,383 (Table 8). This fragment was predicted to contain the DNA encoding $U_L$47 aa 300–696, intervening DNA, and then aa 1–71 of $U_L$46. Analysis of the 5'-vector-insert junction in C:2:C10:B9 revealed out-of-frame translation of the initial $U_L$47 DNA. The insert is expected to contain the $U_L$46 promoter. The epitope, therefore, could be encoded by $U_L$46. C:2:C10:B9 also contains potential sites of internal initiation of translation within $U_L$47. $U_L$46 and $U_L$47 were assayed separately in the COS-7 cotransfection assay (Table 9). $U_L$47 was active, whereas $U_L$46 was not. Truncation analysis localized the epitope to aa 535–590 (Table 9).

Figure 5:
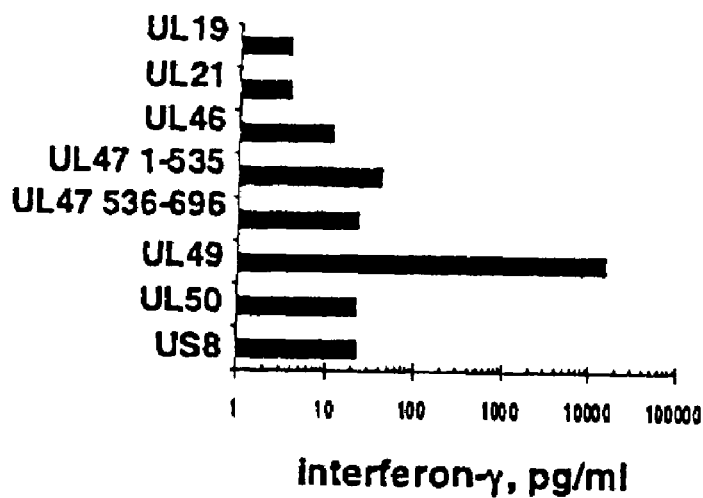
FIG. 5 shows secretion of IFN-γ by lesion-derived CD8$^+$ T cell clone 5491.2000.48 in response to COS-7 cells co-transfected with HLA B*0702 cDNA and the indicated HSV-2 DNA fragments. All HSV-2 genes are full length except for $U_L47$, which is was tested in two segments encoding the indicated amino acids. Values are mean of duplicate IFN-γ secretion into the medium as measured by ELISA.

The specificity of CD8 clone 5491.2000.48 was determined with a panel of partial- and full-length HSV-2 genes. The HSV-2 genes studied were previously shown to be recognized by CD4 T cell clones (See U.S. Pat. No. 6,375,952, issued Apr. 23, 2002). Only HSV-2 $U_L$49, when cotransfected with HLA B*0702, stimulated IFN-γ release by clone 5491.2000.48 (FIG. 5).

Figure 6:
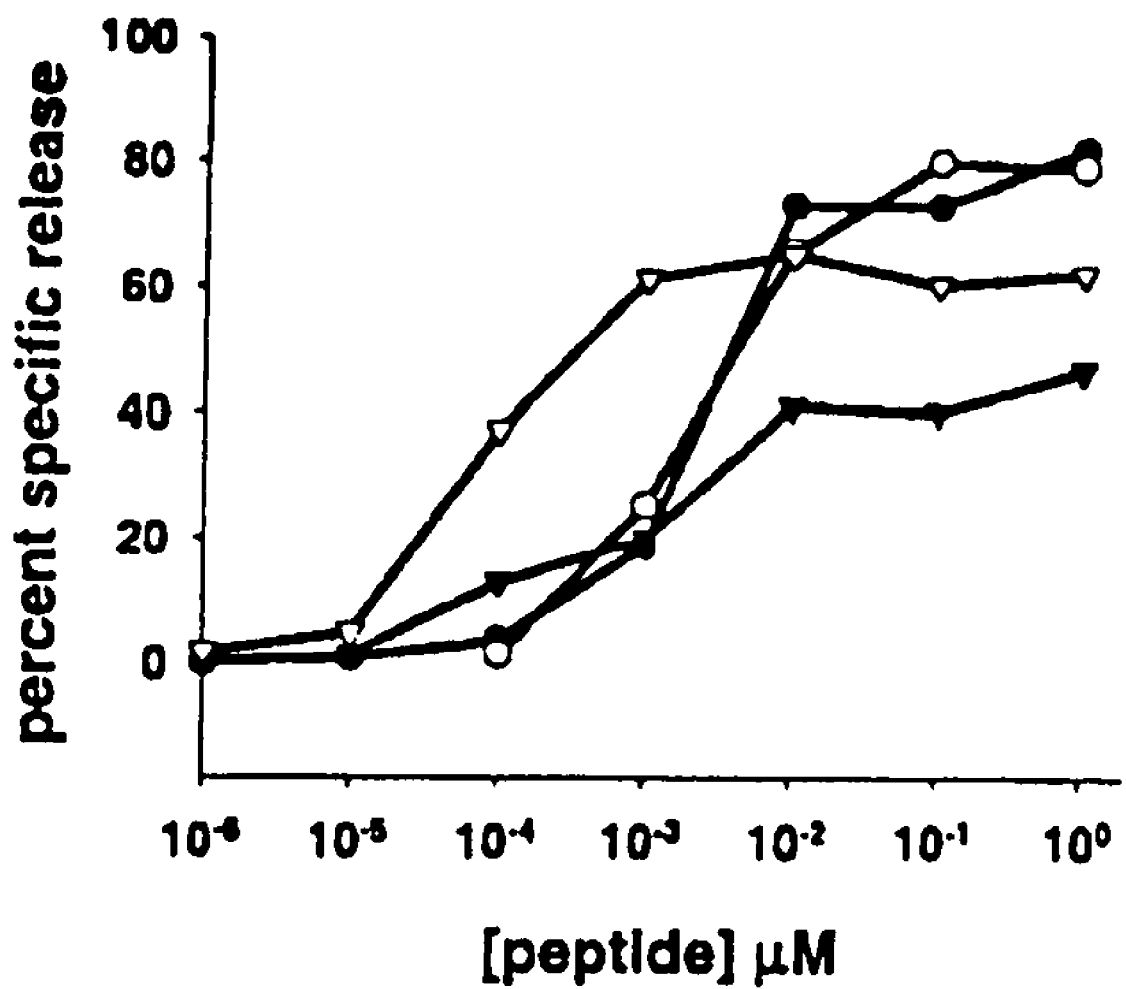
FIG. 6 shows lysis by lesion-derived CD8 clones of autologous LCL loaded with HSV-2 peptides at the indicated concentrations. Data are percent specific $^{51}$Cr release at E:T 20:1. ●, Lysis by clone 5101.1999.23 of targets loaded with $U_L47$ 551–559; ○, clone 1874.1991.22 and $U_L47$ 289–298; ▼, clone 1874.1997.51 and ICP0 92–101; ∇, clone 5491.2000.48 and $U_L49$ 49–57. Lysis of mock-loaded targets was <5% specific release for each clone.

HSV-2 gene $U_L$47 encodes protein VP13/14, whereas $U_L$49 encodes VP22; both tegument proteins are loaded into the cytoplasm on virion binding and entry. The small genomic HSV-2 fragment of $U_L$47 recognized by clone 5101.1999.23 was scanned for peptides fitting the A*0201 binding motif (http://134.2.96.221/and http://bimas.dcrt.nih.gov/molbio/hla_bind/). Peptide $U_L$47 (HSV-2) 289–298 had a 50% effective concentration ($EC_{50}$) in the 1–10 nM range in cytolysis assays (FIG. 6). $U_L$47 535–590 (Table 9) was similarly analyzed. Peptide 551–559 was active at 1 nM (FIG. 6). Potential HLA B*0702-binding peptides in $U_L49$ of HSV-2 were synthesized, and two (aa 47–55 and 14–22) were active at 1 µM. Titration (FIG. 6) showed that $U_L49$ 49–55 was highly active, with an $EC_{50}$ of <10 nM, whereas $U_L49$ 14–22 had activity only at 1 µM. The antigenic peptides in $U_L47$ and $U_L49$ contain significant amino acid sequence differences from the corresponding predicted HSV-1 peptides (Dolan, A. et al., 1998, J. Virol. 72:2010; McGeoch, D. J. et al., 1988, J. Gen. Virol. 69:1531), explaining type-specific recognition of HSV-2 (Table 8).

Recognition of Immediate Early HSV-2 Protein ICP0 by CD8 T Cells

For clone 1874.1997.51, positive reactions to plasmid pools were present in each library. The active plasmids in each library contained a genomic Sau3AI fragment from nucleotides 1858–3022 (Dolan, A. et al., 1998, J. Virol. 72:2010). Nucleotide 2007 listed as T in the published sequence was read as C. In addition to 445 bp of 5'-untranslated sequence, all of predicted exon 1, intron 1, and the first 234 bp of predicted exon 2 of ICP0 were present, preliminarily identifying the antigen as ICP0. Because alternative splicing of HSV-1 ICP0 has been documented at both the RNA and protein levels (Weber, P. C. et al., 1999, Virology 253:288; Carter, K. L., B. Roizman, 1996, Proc. Natl. Acad. Sci. USA 93:12535), the Ag-encoding mRNA species was first identified in COS-7 cells to determine how the ICP0 genomic clone was spliced in this system. COS-7 cells were transfected with genomic clone C:1:H3:B8 (Table 8), and cDNA was synthesized from total cellular RNA followed by PCR designed to amplify the spliced transcript. The size of the PCR product (~300 bp) was consistent with the splicing out of intron 1. Sequencing showed a slight difference from the reported splice point for mature HSV-2 ICP0 mRNA. Three base pairs encoding aa Q26 were missing. Q26 was retained for peptide numbering (below). To determine whether the antigenic peptide lay within exon 1 or exon 2, PCR was repeated with specific primers. The exon 1-partial exon 2 cDNA, but not exon 1 cDNA, was stimulatory for T cell clone 1874.1997.51 (Table 9), localizing the epitope to aa 26–105 in exon 2. Reactivity was confirmed in CTL assays using a recombinant vaccinia virus expressing ICP0. At E:T 20:1, lysis of vaccinia ICP0-infected target cells was 52.1% compared with 2.3% for vaccinia wild type.

Two reported HLA B45-restricted epitopes, AEEAAGIGIL (SEQ ID NO: 14) and GAETFYVDGA (SEQ ID NO: 15), share with the B44 supertype a preference for negatively charged and hydrophobic amino acid side chains at the P2 and P9 anchor positions. ICP0 (HSV-2) 92–105, containing this motif, was active at 1 µM. Truncation yielded ICP0(HSV-2) 92–101, with an $EC_{50}$ in the 1 nM range (FIG. 6).

Recognition of Skin-Derived Fibroblasts and Keratinocytes by CD8 CTL Clones

Within lesions, HSV-2 is mainly present in keratinocytes. How MOI (amount of virus), time of infection, and pretreatment with IFN-γ influenced lysis of dermal fibroblasts and keratinocytes was investigated. For fibroblasts (FIG. 7), in the absence of IFN-γ pretreatment, infection for 2 h led to detectable lysis, which increased with increasing MOI. Lysis was undetectable (<5% specific release at E:T of 20:1) after overnight infection with MOI 1, 5, or 25. With IFN-γ pretreatment, lysis was generally increased, but 2-h infection was still superior. HLA-mismatched target cells were not lysed, even after peptide loading.

Figure 7:
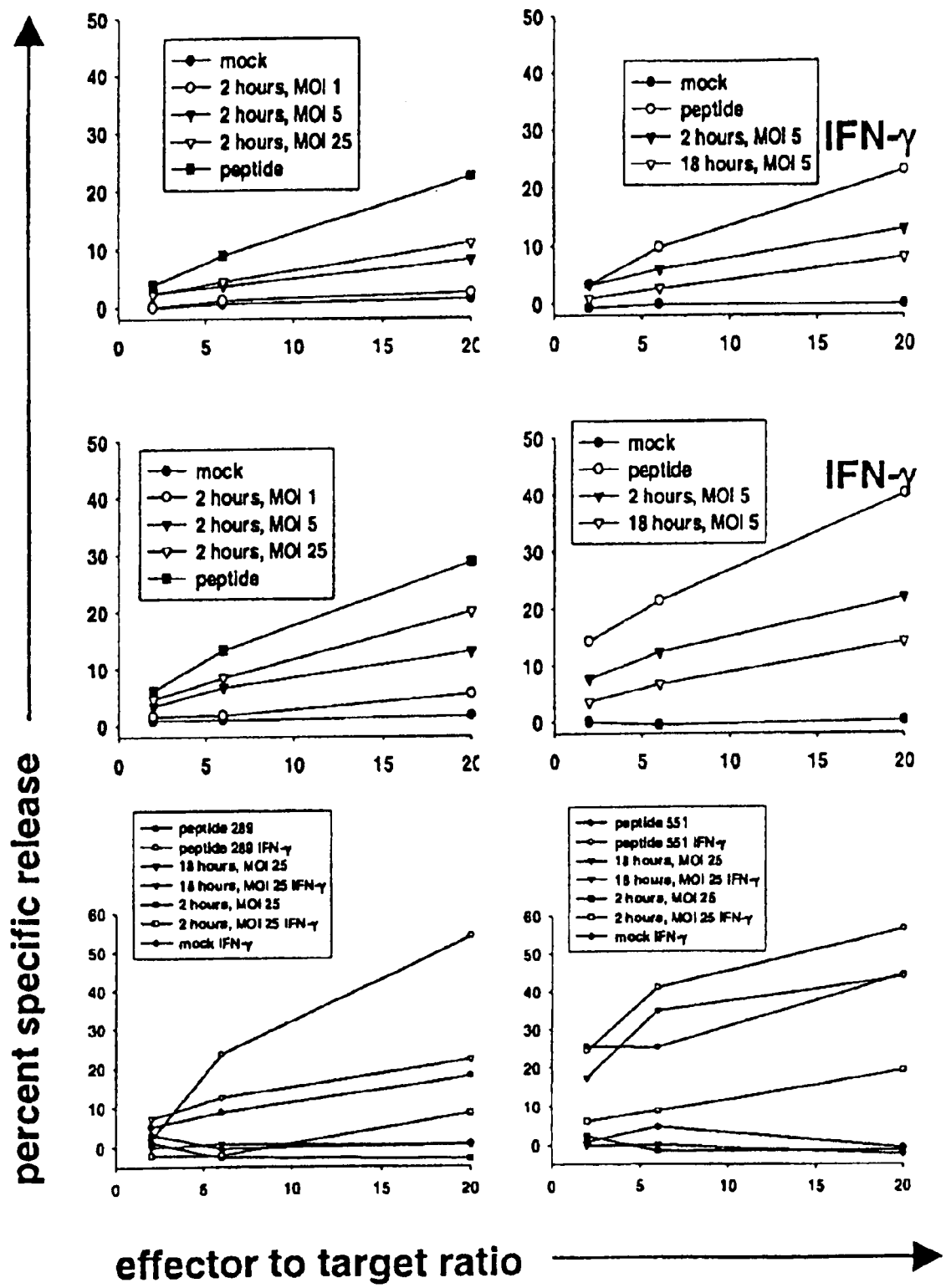
FIG. 7 shows cytolytic activity of CD8 CTL clones against cutaneous cells. Top, $U_L49$-specific clone 5491.2000.48, HLA B*0702-expressing fibroblasts from subject SJ, and peptide $U_L49$ aa 49–47. Middle, $U_L47$-specific clone 1874.1991.22, HLA A*0201-bearing fibroblasts from subject 1874, and peptide $U_L$ 47 aa 551–559. Left, Lysis of non-IFN-γ-treated fibroblasts infected at the indicated MOI for 2 h before assay; right, fibroblasts pretreated for 3 days with 500 U/ml IFN-γ and then infected or treated with peptide. In each case, HLA-mismatched target fibroblasts had <5% specific release at E:T 2:1, 6:1, and 20:1. Bottom, HLA A*0201-bearing keratinocytes are used as target cells. Left, $U_L$ 47-specific clone 5101.1999.23 and peptide $U_L$ 47 aa 289–298; right. $U_L$ 47-specific clone 1874.1991.22 and peptide $U_L$ 47 aa 551–559. HLA A*0201-bearing keratinocytes were mock treated or treated with 500 U/ml IFN-γ and then infected for 2 or 18 h with HSV-2 at MOI 25 or loaded with peptide for 90 min.

Keratinocytes showed some similarities and differences from fibroblast as target cells (FIG. 7). IFN-γ pretreatment generally increased recognition, without leading to lysis of control cells. In contrast to fibroblasts, 18-h infection was generally required. Weak cytolysis of cells infected for 2 h was noted only for IFN-γ-pretreated targets. Chromium release again correlated directly with the amount of infectious virus added, because no specific lysis was noted at MOI 1 or 5.

TAP Dependence of Ag Processing for Recognition by HSV-2 Tegument Protein Epitopes by CD8 CTL For each of the three CD8 clones studied, lysis of TAP-deficient cells after HSV-2 infection was greatly reduced in comparison to wild-type EBV-LCL (Table 10). Greater than 90% of each of the TAP-deficient cell lines, as well as control wild-type LCL, were permissive for viral infection and protein synthesis as evaluated by flow cytometry using mAb specific for envelope glycoprotein gD. Peptide loading was able to sensitize the TAP-deficient cells, confirming HLA class I expression.

TABLE 10

TAP dependence of processing of HSV-2 tegument for presentation to CD8 T cells[1]

| Target Cells | Mock | Peptide | HSV-2 |
|---|---|---|---|
| CD8 clone 1874.1991.22 Controls | | | |
| 1874 | 2.5 | 54.8 | 30.7 |
| 5491 | 2.0 | −2.5 | −1.2 |
| TAP (−) | | | |
| 721.174 | −3.9 | 90.0 | 1.3 |
| T2 | 0.7 | 94.7 | 2.2 |
| CD8 clone 5101.1999.23 Controls | | | |
| 1874 | 0.8 | 52.5 | 18.2 |
| 5491 | 1.7 | −2.1 | −1.2 |
| TAP (−) | | | |
| 721.174 | 0 | 31.7 | 2.9 |
| T2 | −0.7 | 71.0 | 0.8 |
| CD8 clone 5491.2000.48 Controls | | | |
| 1874 | 0.8 | −2.7 | 3.6 |
| 5491 | 0.2 | 68.3 | 21.2 |
| TAP (−) | | | |
| T2/B7.63 | −0.4 | 57.8 | 3.4 |
| T2 | 0.2 | 0.4 | 3.6 |

[1]Data are percent specific release in $^{51}Cr$ release assays at E:T 20:1. The first two clones are HLA A*0201-restricted. Lysis of the A*0201-bearing wild-type EBV-LCL 1874, but not non-A*0201 EBV-LCL 5491, was detected after peptide loading ($U_L47$ 551–559 for clone 1874.1991.22; $U_L47$ 551–559 for clone 5101.1999.23; 1 µM, 90 min) or HSV-2 infection (MOI 10, 18 h). In contrast, peptide loading, but not HSV-2-infection, was able to sensitize TAP-deficient cell lines. Similar data are shown for the third clone, a HLA B*0702-restricted, $U_L49$-specific CTL clone and peptide $U_L49$ 49–57, using the B*0702 autologous EBV-LCL, 5491, the non-B*0702 EBV-LCL, 1874, and the TAP-deficient, HLA B*0702-containing transfectant T2/B7.63. As an additional control, T2 cells, which do not express B*0702, were not lysed after peptide loading.

Discussion

HSV-2 causes considerable morbidity and mortality, especially in neonates. Because of the chronic nature of the infection, the limitations of antiviral therapy, and the frequency with which transmission is caused by asymptomatic shedding of the virus, vaccination is likely to be required to reduce new HSV-2 infections. The recent report that vaccination with a specific adjuvant and an envelope glycoprotein induced partial protection in HSV-1/HSV-2-seronegative women highlights both the potential efficacy of vaccination and the need for improved formulations and markers of effective immunity.

Little is known about the specificity of human HSV-2-specific CD8 CTL. The two published epitopes are type-common peptides within glycoproteins B and D. At the nonclonal level, experiments using restimulation of PBMC, drug blocks, and vaccinia recombinants show that HSV-1 ICP4, ICP27, ICP0, all immediate early proteins, HSV-1 early protein ICP6, and possibly other true early proteins may be targets of human CTL. HSV-1 early protein thymidine kinase (tk) is recognized by CD8 clones from PBMC of subjects treated with tk-transfected autologous cells, but this is likely a primary immune response. A PBMC-derived CD8 T cell clone specific for a melanoma-associated protein (Melan A/MART-1) also reacted with a peptide from HSV-1 glycoprotein C.

$U_L49$ encodes VP22, a tegument protein required for viral replication. $U_L49$ protein is also abundant in virions and delivered into the cytoplasm by virus entry. Lysis of EBV-LCL by tegument-specific CD8 CTL was not inhibited by blockade of gene transcription or infection with a replication-incompetent virus, consistent with the processing and presentation of preformed virion input protein.

TAP-independent processing has been reported in other viral systems. The examination of three discrete epitopes in tegument proteins did not reveal evidence for TAP-independent Ag processing of HSV epitopes. The CD8 response seems to "evade the evasion," at least in the cases examined to date, while continuing to rely on TAP for Ag processing.

Most studies of clonal CD8 responses have used EBV-LCL as target cells. These cells are relatively resistant to HSV-mediated class I down-regulation. For dermal fibroblasts, it was found that a short time of infection (2 h) was adequate for target cell sensitization for lysis by tegument protein-specific CTL. Because the $U_L47$ and $U_L49$ tegument proteins are synthesized with "late" kinetics, typically starting after 6 h or more of viral infection, these data are also consistent with recognition of preformed Ag in fibroblasts. Lysis was MOI dependent. Because HSV preparations typically contain a large number of defective particles, it is likely that tegument proteins were also being delivered into fibroblasts by noninfectious particles. After 18 h of infection, the fibroblasts were not lysed, regardless of MOI, similar to previous results with CD8 CTL clones of unknown fine specificity. IFN-γ pretreatment was able to partially restore lysis of 18-h-infected cells. In contrast to fibroblasts, recognition of keratinocytes after 18 h of infection was superior to recognition after 2 h of infection. The reason for the difference between fibroblasts and keratinocytes is unknown. IFN-γ pretreatment was able to restore some lysis of 2-h-infected cells, and further improved recognition of 18-h-infected cells.

Tegument proteins have not previously been described as targets of the HSV-specific CD8 T cell response. CD4 responses to HSV-1 $U_L47$ have been detected in HSV-mediated acute retinal necrosis. CD4 responses to $U_L49$ are commonly detected among lesion-infiltrating HSV-2-specific clones. Because responses to $U_L49$ are also present in the cornea in herpes stromal keratitis in humans, a disease that may be driven by pathogenic Th1-like T cells, caution is warranted in using this protein as a vaccine. Overall, $U_L49$ is the only known HSV-2 protein recognized by both CD4 and CD8 T cell clones recovered from herpetic lesions. A unique intercellular transport pathway allows highly efficient uptake of soluble $U_L49$ protein into a variety of epithelial cell types which could also intersect antigen processing pathways.

In summary, reactivity of lesion-infiltrating, HSV-2 type-specific CD8 T cell clones with the tegument proteins encoded by genes $U_L47$ and $U_L49$ (VP13/14 and VP22, respectively), and ICP0, are described for the first time. The data are consistent with a modulatory effect of ICP47 and/or vhs on the CD8 response to HSV. TAP function, but not viral gene transcription, is required for recognition by $U_L47$- and $U_L49$-specific clones, consistent with processing of preformed virion input protein. Tegument-specific CD8 clones were able to recognize skin-derived fibroblasts and keratinocytes. Responses were also detectable in the PBMC of additional subjects.

Example 5

HSV-2 15-mer Peptide Screening with CD8+ T Cells

HSV-2 seropositive donors were obtained (AD104, AD116, AD120, D477, HV5101, JH6376, EB5491, TM10062). Donors HV5101 and EB5491 experience frequent anogenital lesion recurrences. Donors JH6376 and TM10062 experience few or no anogenital lesion recurrences. Leukopheresis PBMC were obtained from each donor after informed consent. Donor PBMC were HLA-typed by low resolution DNA typing methodology. Synthetic peptides (15 amino-acids in length and overlapping in sequence by 11 amino-acids) were synthesized that spanned the following HSV-2 polypeptides: $U_L47$ (aa 1–696), $U_L49$ (aa 1–300), ICP27 (aa 1–512). Peptides (5 mg each) were delivered in lyophilized form in glass vials and dissolved at a concentration of 10 mg/ml in DMSO, transferred to sterile cryovials and stored at −20 degrees C. The peptides were screened with CD8+ T cells purified from adherent macrophage-depleted PBMC. CD8+ T cells were purified by depletion of non-CD8+ cells using a commercial MACS bead kit (Miltenyi). CD8+ T cells purified in this manner were generally >95% CD8+CD3+CD4−, as measured by flow cytometry (FACS). Peptides were screened by 24-hour co-culture of CD8+ T cells (2×10e5/well) and autologous dendritic cells (1×10e4/well) and peptides (10 μg/ml each) in 96-well ELISPOT plates that had been pre-coated with anti-human IFN-g antibody 1D1K (mAbTech). Peptides were initially screened as pools of >/=10 peptides. ELISPOT plates were subsequently developed per a standard protocol. The number of spots per well was counted using an automated video-microscopy ELISPOT reader. Peptides in pools scoring positive were subsequently tested individually in a second ELISPOT assay. For AD116, the novel peptides $U_L49$/21–35 (#6)and $U_L49$/193–208 (#49) scored positive both pooled and individually. AD116 also recognized the previously described B*0702-restricted epitope $U_L49$/49–57 contained in 15-mer peptides $U_L49$/45–59 (#12) and $U_L49$/49–63 (#13). D477, HV5101, and JH6376 T cells recognized the previously described HLA-A*0201-restricted epitopes $U_L47$/289–297 and $U_L47$/550–559 contained in 15-mers #73/#74 and #137/#138, respectively. EB5491 T cells recognized the previously described B*0702-restricted epitope $U_L49/49$–57 epitope contained in 15-mer peptides $U_L49/45$–59 (#12) and $U_L49/49$–63 (#13). D477 scored positive for peptide pool $U_L49$ (#11–20). TM10062 did not score positive on any peptide pool from $U_L47$ or $U_L49$.

| Donor HLA Types | | | |
|---|---|---|---|
| Donor: | HLA-A | HLA-B | HLA-C |
| AD104 | 24, 33 | 46, 58 | 01, 0302 |
| AD116 | 0206, 24 | 0702, 35 | 0702, 1203 |
| AD120 | 0211, 3303 | 1505, 4403 | 0303, 0706 |
| D477 | 0201, 2501 | 1501, 5101 | 0304, 12 |
| HV5101 | 0101, 0201 | 0801, 57 | 06, 0701 |
| JH6376 | 0201, 03 | 07, 44 | 05, 07 |
| EB5491 | 01, 26 | 07, 08 | 07 |
| TM10062 | 0201, 26 | 14, 27 | 01, 08 |

| CD8+ T cell peptide-screening hits | | | |
|---|---|---|---|
| AD104 US3 #33 | HSV-2 | AIDYVHCKGIIHRDI | (SEQ ID NO: 16) |
| | HSV-1 | AVDYIHRQGIIHRDI | (SEQ ID NO: 17) |
| AD116 UL47 #86 | HSV-2 | AVPLLSAGGAAPPHP | (SEQ ID NO: 18) |
| | HSV-1 | AVPLLSAGGLVSPQS | (SEQ ID NO: 19) |
| UL49 #6 | HSV-2 | ELYYGPVSP-ADPESP | (SEQ ID NO: 20) |
| | HSV-1 | DLYYTPSSGMASPDSP | (SEQ ID NO: 21) |
| UL49 #12 | HSV-2 | PMRARPRGEVRFLHY | (SEQ ID NO: 22) |
| | HSV-1 | QRSARQRGEVRFVQY | (SEQ ID NO: 23) |
| UL49 #13 | HSV-2 | RPRGEVRFLHYDEAG | (SEQ ID NO: 24) |
| | HSV-1 | RQRGEVRFVQYPESD | (SEQ ID NO: 25) |
| UL49 #49 | HSV-2 | VAGFNKRVFCAAVGR | (SEQ ID NO: 26) |
| | HSV-1 | VAGFNKRVFCAAVGR | (SEQ ID NO: 27) |
| HY5101 UL47 #143 | HSV-2 | STAPEVGTYTPLRYAC | (SEQ ID NO: 28) |
| | HSV-1 | FTAPEVGTYTPLRYAC | (SEQ ID NO: 29) |

Figure 9:
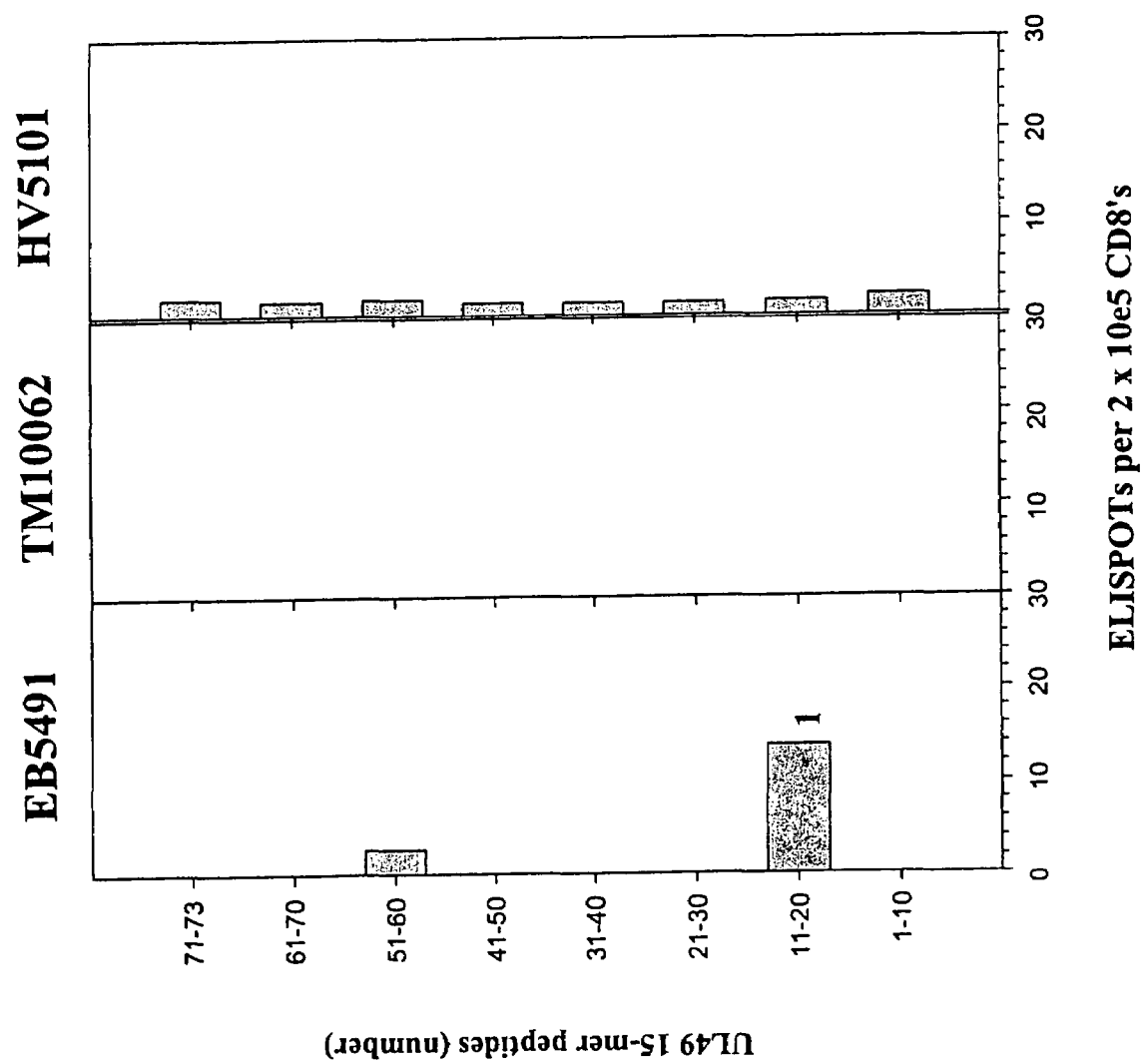
FIG. 9 shows the results of peptide screening for donors EB5491, TM10062 and HV5101.
Figure 10:
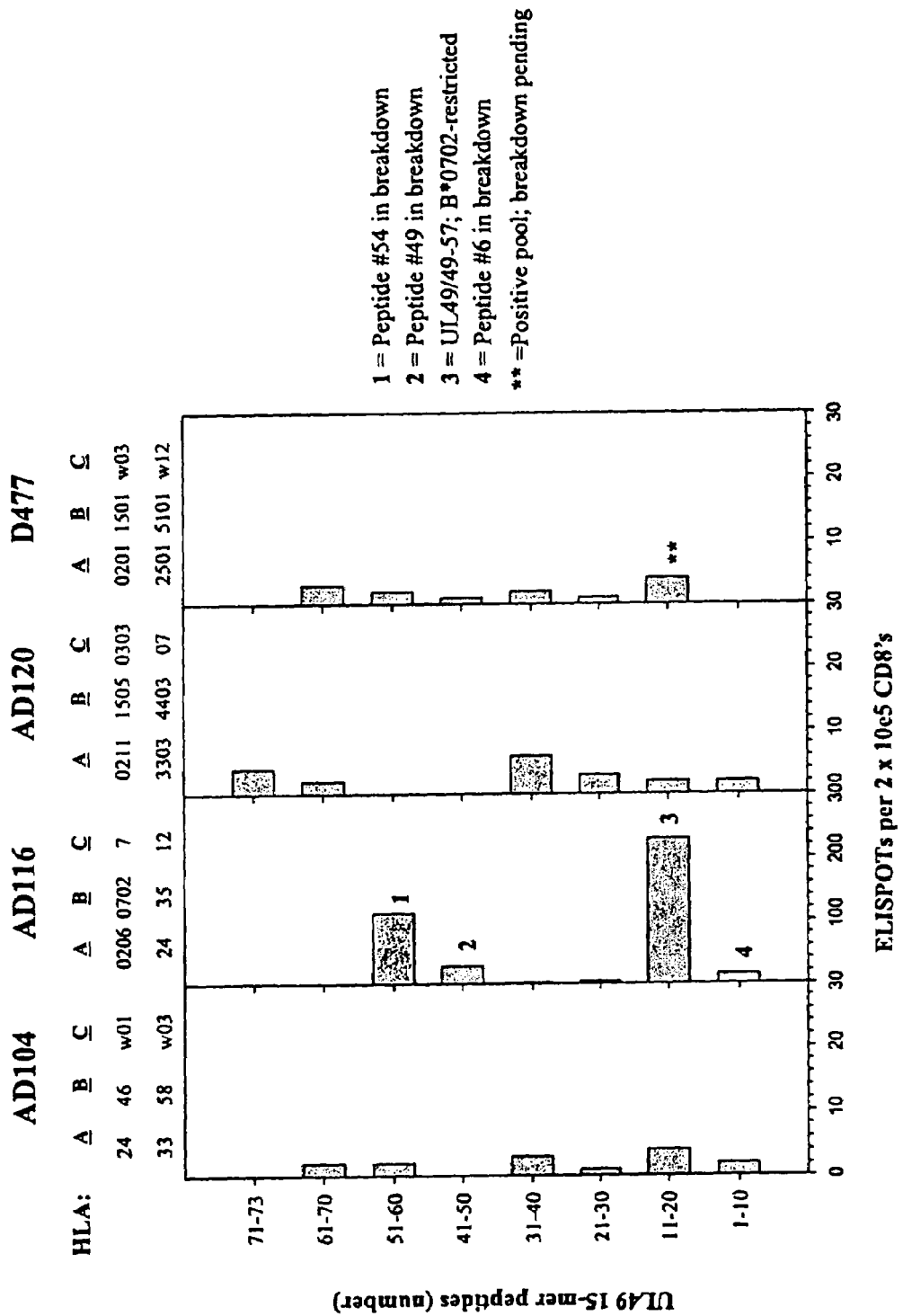
FIG. 10 shows results of peptide screening for donors AD104, AD116, AD120 and D477.

FIG. 8 shows the results for AD116. FIG. 9 shows the results for EB5491, TM10062 and HV5101. The peptide hit indicated with a "1" represents $U_L49$, amino acids 49–57, B*0702-restricted. FIG. 10 shows results for AD104, AD116, AD120 and D477. The peptide hit indicated with a "1" represents peptide #54. The peptide hit indicated with a "2" represents peptide #49. The peptide hit indicated with a "3" represents $U_L49$, amino acids 49–57, B*0702-restricted. The peptide hit indicated with a "4" represents peptide #6.

Example 6

Detection of HSV-Specific T-Cell Responses in Cervical Lymphocytes

Mucosal immune responses are segregated from PBMC, and localization of HSV-specific CTL to the mucosa of mice is associated with protection from vaginal inoculation. This example demonstrates that HSV-specific T cells, including CD8+ cells, can be detected in cervical lymphocytes.

Cells from a representative cervical cytobrush specimen were collected during an active genital HSV-2 outbreak and expanded in bulk with PHA/IL-2, and subsequently analyzed for HSV-specific proliferative and cytotoxic responses. Proliferation and cytotoxicity assays used autologous PBMC or LCL as APC as described above for skin-derived lymphocytes. Anti-HLA class I nab W6/32 or anti-HLA DR mAb L243 were used as described (Koelle DM et al., J. Virol. 1994, 68:2803–10; Koelle DM et al., J. Infect. Dis. 1994, 169:956–61). Antigen-specific proliferative responses and cytotoxic responses were present. Fractionation and mAb inhibition studies show a contribution of CD8 CTL to the cytotoxic response.

Example 7

Detection of HSV-Specific T-Cell Responses in Primary Genital HSV-2 Lesions

In this example, biopsy specimens were collected from a patient presenting with symptoms consistent with primary genital HSV-2 infection. The phenotypes of the collected cells were determined, and LIL and PBMC from the specimens were subjected to proliferative and cytotoxicity assays. The results show that the HSV-specific proliferative and cytotoxic responses of CTL present in primary genital HSV-2 lesions are typical of those detected during recurrent disease.

CW7477 developed dysuria, fever, buttock, and lower abdomen lesions three days after his last sexual contact. Lesions lasted 13 days and grew HSV-2. Acyclovir treatment was begun on day four of symptoms. Biopsies were done on days four and seven. Serostatus was atypical positive (only a few bands present on immunoblot) at day four, with more bands, but still less than most convalescent sera, on day 26, by enhanced chemiluminescence (ECL; Dalessio J. and Ashley R., J. Clin. Microbiol. 1992, 30(4): 1005–7) variant of type-specific HSV-2 immunoblot. The clinical and laboratory data were consistent with primary genital HSV-2 infection. Biopsy specimens were obtained on day four and seven of symptoms and bulk LIL expanded with PHA/IL-2 as described above.

The phenotype of the expanded cells was split between CD4 and CD8 cells, with 15–25% CD3+/CD16,56+ cells and 5–10% TCR γδ+ cells in the LIL. In comparison, cells from normal skin had almost no CD16,56 (+) events and no TCR γδ cells. The nature of the CD3+/CD16,56+ cells is unknown but these are frequently seen in expanded LIL. The antibody cocktail has a combination of αCD16-PE and αCD56-PE.

The HSV-specific proliferative and cytotoxic responses were fairly typical of those detected during recurrent disease (Koelle DM et al., J. Clin. Invest. 1998; 101:1500–1508). Cross-reactive responses to HSV-1 and HSV-2 were present, as were antigen-specific responses to HSV glycoproteins. Normal skin responses were low, and PBMC responses were developing by day 15.

Example 8

Identification of an ICP0 Antigen Recognized by HSV-Specific CD8 CTL

This example demonstrates, via expression cloning, the antigenicity of ICP0. In particular, an epitope within amino acids 92–101 of ICP0 is identified. In addition, the antigenicity of ICP0 is confirmed using vaccinia. The amino acid numbering uses the nomenclature and numbering of Dolan et al., J. Virol 1998, 72:2010–21. The methods used herein are described in U.S. Pat. No. 6,413,518, issued Jul. 2, 2002.

Results

All HSV-specific CD8 clones released IFN-γ in a specific manner. In addition, the utility of the interferon-gamma assay was examined as a confirmatory test for HLA restriction. Clone RW51 specifically released interferon-gamma after exposure to Cos-7 cells transfected with HLA B*4501, but not with A*0201, and infection with HSV-2.

TABLE 12

Secretion of interferon-gamma of CD8 TCC RW51 in response to Cos-7 cells transfected with various DNAs (or peptide loaded at 1 μM) measured by ELISA in pg/ml. Responses of $5 \times 10^4$ TCC to $7 \times 10^3$ Cos-7 cells checked at 24 hours.

| HLA class I cDNA | empty vector | pool A1:H3 | clone A1:H3: B8 | ICP0 exon exon 1 | ICP0 exon 1, 2 | ICP0 92–105 |
|---|---|---|---|---|---|---|
| empty vector | not done | not done | <2 | <2 | <2 | <2 |
| B*4501 | <2 | 420 | >600 | <2 | >600 | 1,100 |

Figure 12:
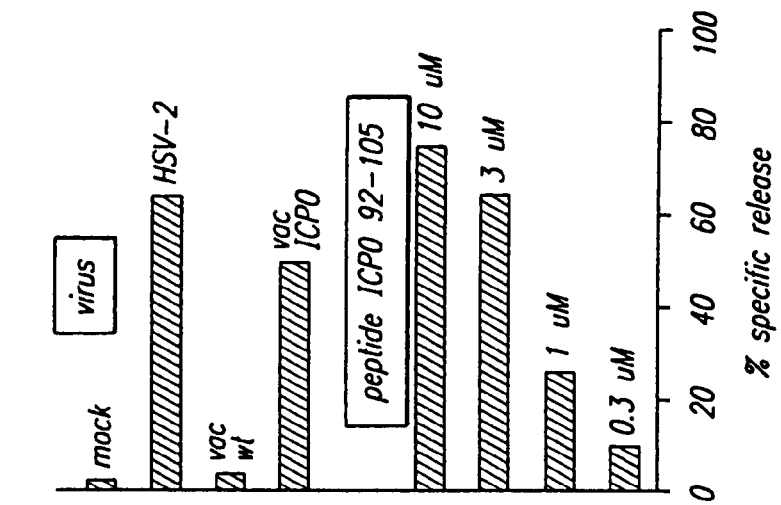
FIG. 12 is a bar graph showing CTL activity of RW51 against vaccinia ICP0 and indicated concentrations of synthetic ICP0 92–105. Four-hour $^{51}$Cr release assay with effector:target ratio 10:1. Spontaneous release all <20%.
Figure 11:
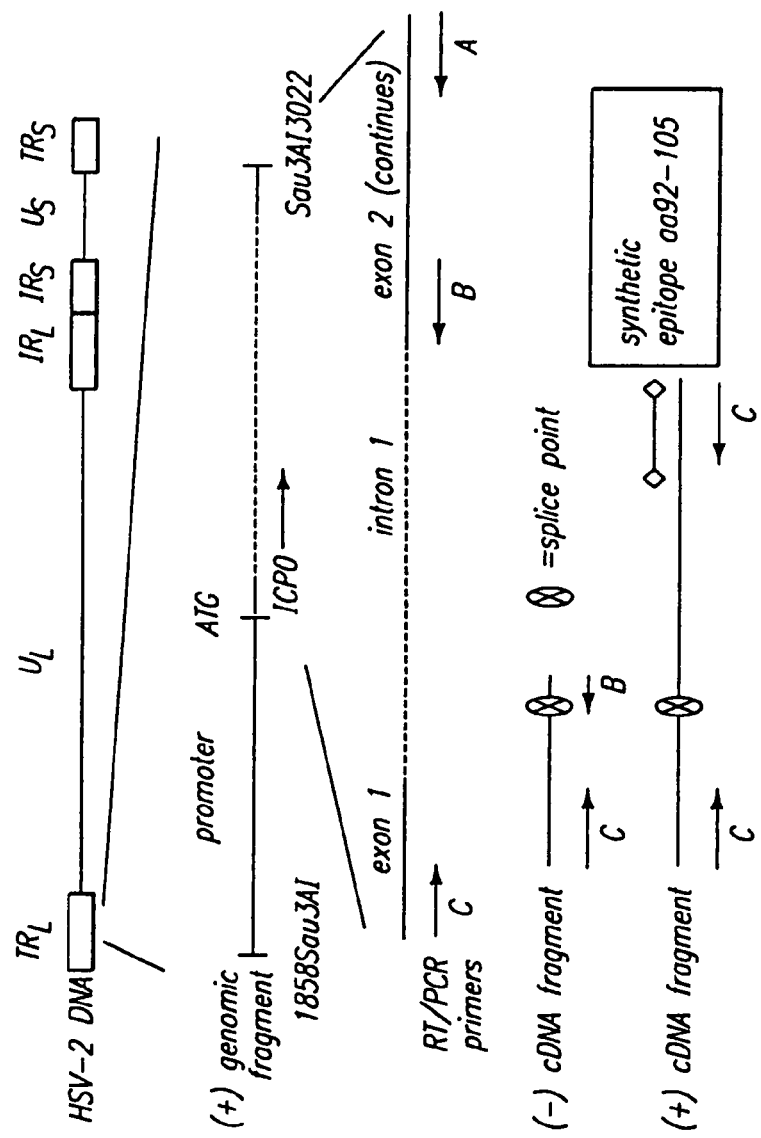
FIG. 11 is a schematic representation of the positive genomic clone isolated from Sau3A I library of HSV-2 DNA (second line), which contained part of the ICP0 gene. The genomic clone was transfected into cells and primer A used for cDNA synthesis. The exon-1/exon2 C-A (fifth line) and HLA B45 cDNAs stimulated interferon-gamma secretion from T cell clone (TCC) RW51 after transfection into Cos-7 cells. Exon-1 B-C cDNA (fourth line) was negative.
Figure 13:
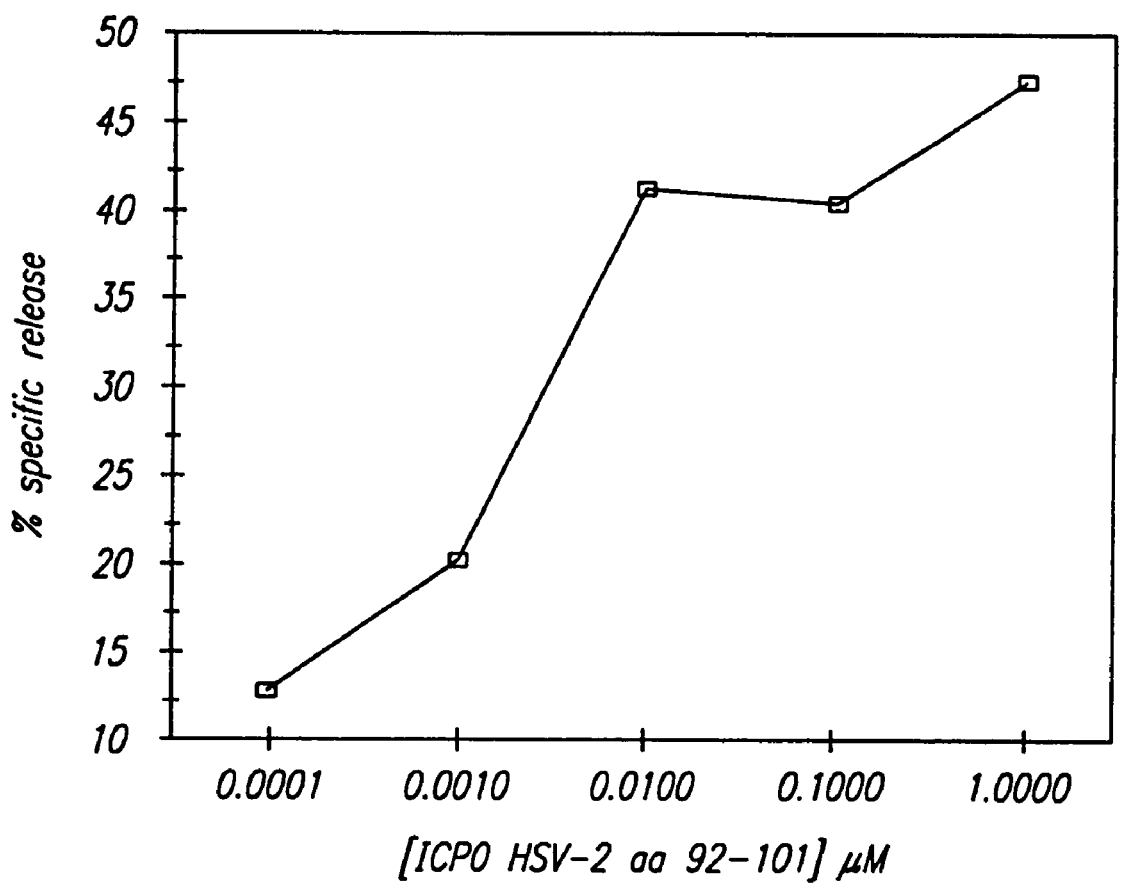
FIG. 13 is a graph showing CTL activity of RW51 against indicated concentrations of synthetic ICP0 92–101. Four-hour $^{51}$Cr release assay with effector:target ratio 10:1. Spontaneous release all <20%.
Figure 14:
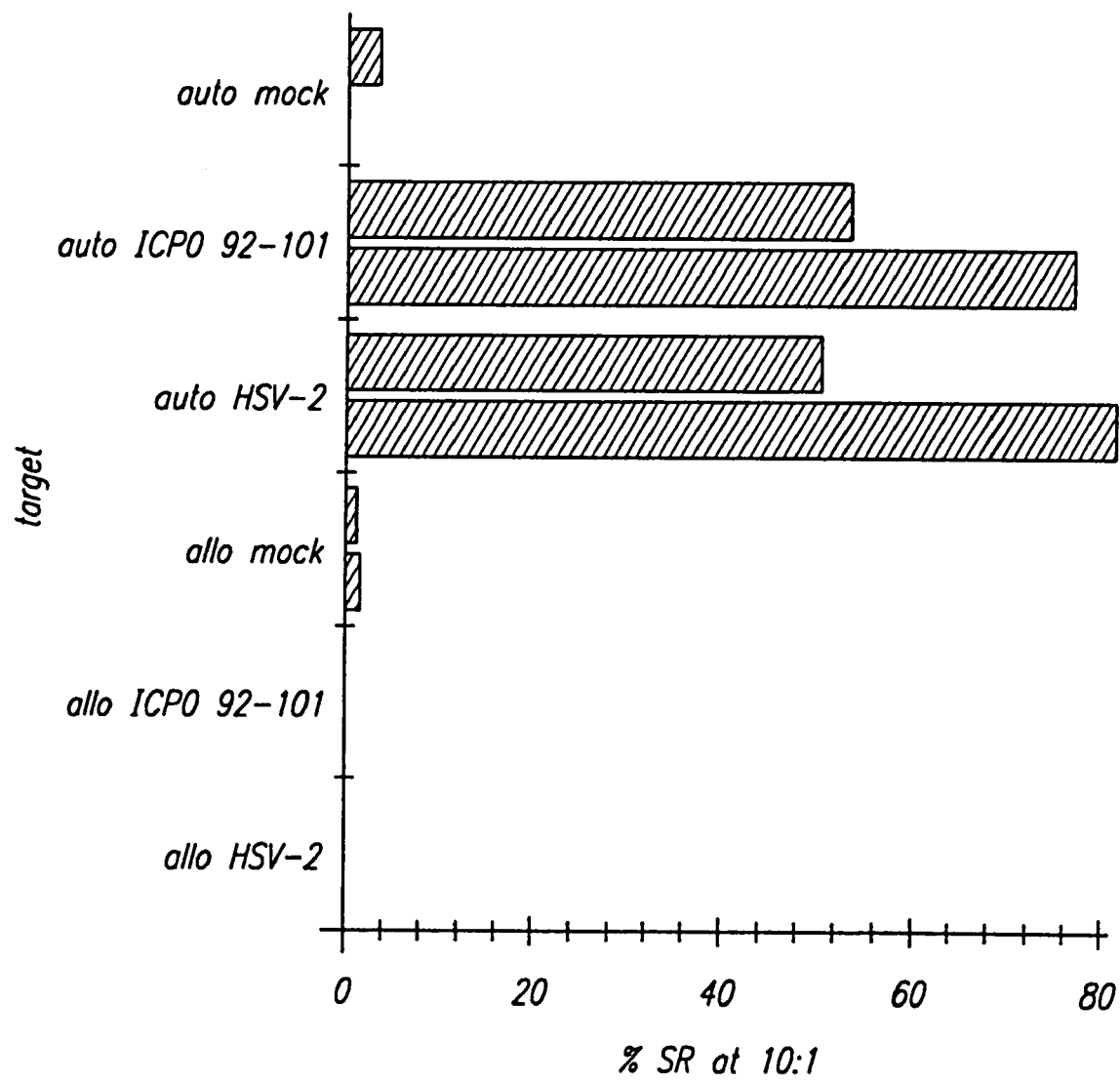
FIG. 14 is a graph showing CTL activity of lymphocytes subject RW, derived from peripheral blood and stimulated with a peptide of HSV-2 ICP0 amino acids 92–101. Four-hour $^{51}$Cr release assay with effector:target ratio of 10:1. Spontaneous release <20%. For each pair of bars, the upper bar represents data from a lesion-derived CD8 clone and the lower bar represents data from PBMC stimulated with peptide.
Figure 15:
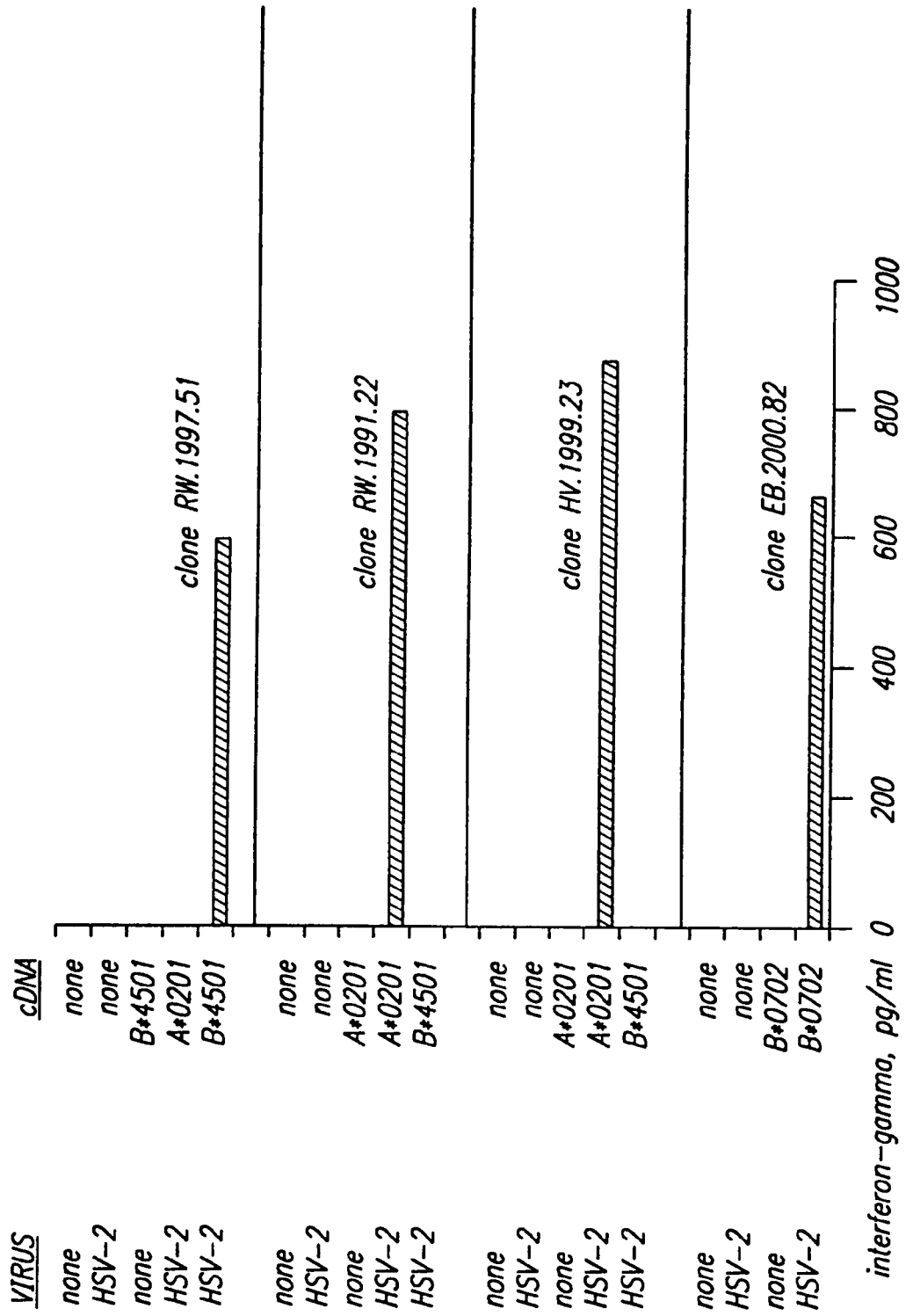
FIG. 15 shows confirmation of HLA restricting allele, HSV-2 reactivity, and IFN-gamma secretion by lesion CD8 clones.
Figure 16:
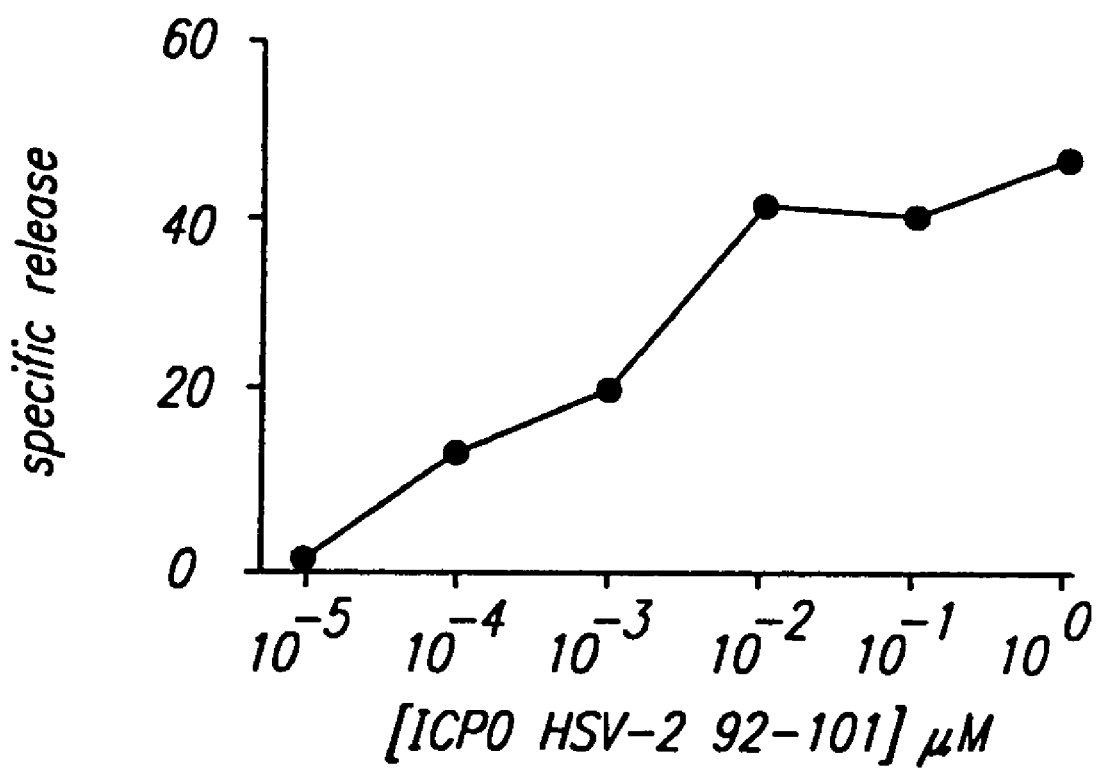
FIG. 16 shows peptide dose-response for lesion CD8 clone RW.1997.51 worked up by expression cloning.
Figure 17:
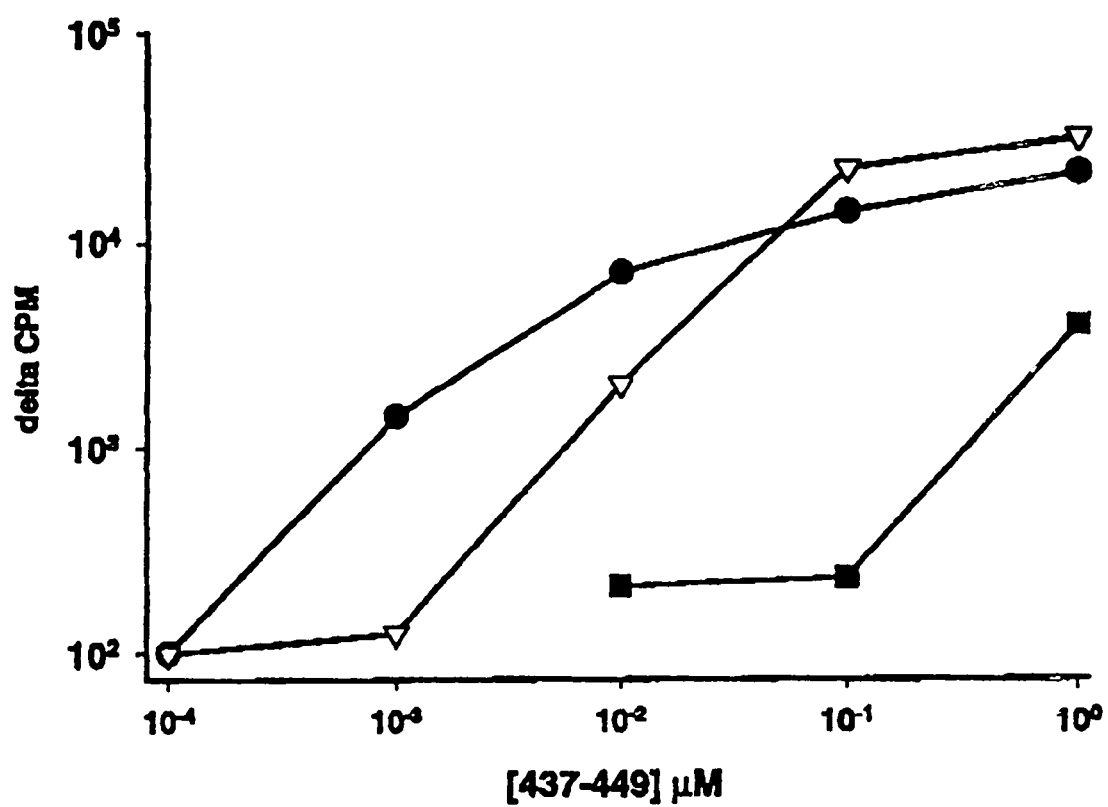
FIG. 17 is a line graph showing HLA restriction element for T-cell clone BM.17 response to peptide 437–449 of VP16 ($U_L48$) of HSV-2. Proliferative responses are plotted versus concentration of viral peptide. Antigen presenting cells are EBV-LCL that are either autologous (closed circles), homozygous for HLA DQB1*0501 (open triangles), or homozygous for HLA DQB1*0201 (squares).

To choose peptides efficiently, a HLA B45 binding motif was derived from B45-restricted peptides, and pool sequence from peptides eluted from B*4501. The motif is glutamic acid at position 2, hydrophobic at position 10 (P1 and P9 in "binding" nomenclature (Rammansee H-G, Current Opinion in Immunology 1995, 7:85–96)). Peptide ICP0 92–105 (AERQGSPTPADAQG; SEQ ID NO: 30) was active in CTL (FIG. 14) and interferon-gamma (Table 12) assays. Other candidate exon 2 peptides were not. The high $EC_{50}$ value (~1 μM) may be due to the carboxy-terminus tail predicted to lie outside the peptide-binding groove and reduce binding to HLA B*4501. Vaccinia-ICP0 from B. Rouse (Manickan E et al., J. Virol. 1995, 69:4711–16) was grown and titered (Koelle D M et al., J. Virol. 1994, 68:2803–10). Clone RW51 specifically lysed vac-ICP0 targets (FIG. 12). The availability of the vaccinia was fortuitous, and not required to confirm the result of expression cloning. To narrow down the epitope, a peptide comprising amino acids 92–101 of ICP0 (AERQGSPTTP; SEQ ID NO: 31) was synthesized. The $IC_{50}$ for this peptide is between 1 and 10 nanomolar (FIG. 13).

To confirm that patients with HSV-2 infection have T-cells reactive with the newly discovered T-cell antigen circulating in their peripheral blood, peripheral blood mononuclear cells (PBMC) from the patient from whom the lesion-derived clone RW51 was recovered were peptide stimulated. PBMC were cultured for three days at $2 \times 10^6$ cells per 1.88 cm² well in 2 ml of T-cell medium containing 1.0 μg/ml peptide HSV-2 ICP0 92–101. On the fourth day, IL-2 (32 units/ml) was added. On the eighth day, the cells were washed and restimulated in the same size well with an additional $2 \times 10^6$ autologous, irradiated (3300 rad gamma irradiation) PBMC, 1.0 μg/ml of the same peptide, and IL-2 (32 U/ml).

Responders were cultured for an additional nine days in the presence of IL-2 and expanded as necessary. Cytotoxicity assay was performed using autologous or HLA class I-mismatched LCL treated either with nothing, peptide HSV-2 ICP0 92–101 at 1 μg/ml for 18 hours, or infection with HSV-2 strain 333 at MOI 10 for 18 hours. The cytotoxicity assay was a standard four-hour $^{51}Cr$ release assay.

The results (FIG. 14) show that stimulation of PBMC with peptide HSV-2 ICP0 92–101 was able to stimulate cells with cytotoxicity towards HSV-2 infected cells, and that this activity was not present against HLA class I-mismatched cells. For comparison, the index T-cell clone RW51 was also used as an effector cell in this assay and displayed comparable, although slightly higher, cytotoxicity at the effector to target ratio of 10:1 shown in FIG. 14.

Example 9

Identification of Additional ICP0 Antigens Recognized by HSV-Specific CTL

This example demonstrates, via use of a different population of CD8+ T cells from a different human subject, the specific recognition of amino acids 743–751 by lesion-derived T cells. The recognition event involves HLA allele B*0702, which is relatively common (approximately 10%) in the human population. In addition, amino acids 288–307 of ICP0 have been found to be specifically recognized by lesion-derived T cells.

Example 10

ICP0 Stimulation of CTL Responses in Additional HLA-B45 Subjects

This example demonstrates that other HLA-B45 positive donors have detectable CD8+ T cell responses to the previously defined ICP0 92–101 peptide.

Peptide restimulation in bulk format are appropriate for sensitive detection of CTL, while lesion derived antigen (LDA) formats yield CTL levels, but require prolonged cell replication for detection. In this example, $4 \times 10^6$ PBMC in 2 ml T-cell medium were stimulated with 1 μg/ml HSV-2 peptides, and IL-2 (10–30 U/ml) was added on day 3. On day 8, responders were washed and restimulated in 2 ml with $2 \times 10^6$ autologous irradiated PBMC, fresh peptide, and IL-2, and split as necessary until assay on day 14–16. For two HLA B*4501-bearing persons including the index subject, convincing HLA class-restricted CD8 CTL were detected that not only lysed peptide-loaded targets, but also killed HSV-2-infected targets and were inhibited by anti-class I mAb (Table 13).

TABLE 13

Lysis of HLA B*4501 LCL by PBMC stimulated with peptide HSV-2 ICP0 92–101, or (+) control clone RW.1997.51. Results are percent specific release in four-hour CTL assays at effector to target ratio of 10:1–20:1.

| Effector | target[1] | | | | | | |
|---|---|---|---|---|---|---|---|
| | RW mock | RW peptide[1] | RW HSV-2 | RW HSV-2/ anti-class I[2] | HV mock | HV peptide | HV HSV-2 |
| RW PBMC | 1 | 45.3 | 48.2 | 12.2 | 0 | −1 | 0 |
| PO PBMC | 0 | 54.9 | 33.5 | 5.8 | 4 | −1 | 0 |
| clone RW.1997.51 | 0 | 65.3 | 67.3 | 5.2 | 1 | 0 | 2 |

[1]Target LCL (RW = B*4501, HV = not B*4501) loaded with 1 μg/ml ICP0 92–101 for 90 minutes, or HSV-2 infection, MOI 5, 18 hours.
[2]Anti-HLA class I mAb W6/32 included at 10 μg/ml.

Example 11

Definition of Additional T-Cell Epitopes in Tegument Protein $U_L48$ (VP16)

Three epitopes within VP16, all HSV-2 type-specific were previously identified (K. R. Jerome et al., 1998, J. Virol., 72:436–441), and proliferative responses to full-length VP16 in bulk cultures of genital HSV-2 lesion-infiltrating lymphocytes from four of seven (57%) patients were detected (D. M. Koelle et al., 1998, J. Clin. Invest., 101: 1500–09). Additional peptide epitopes were sought within VP16 by two strategies. The first strategy involved screening panels of clones recovered from lesion vesicle fluid for reactivity with recombinant VP16 of HSV-2 followed by epitope mapping with peptides. Peptides containing amino acids 185–197 and the overlapping pair 209–221 and 213–225 were stimulatory for TCC RH.13 and KM.7, respectively. All other VP16 peptides tested were negative (<500 cpm). The second strategy involved using PBMC as starting material and secondary in vitro stimulation with recombinant baculovirus-derived VP16. Clones (BM.17 and SB.17) from two individuals recognized the same peptide (amino acids 437–449) as well as β-gal-VP16 fusion protein and whole virus. All three newly defined VP16 epitopes were type-common, shared by HSV-1 and HSV-2 whole virus preparations, as expected from sequence data (A. Cress and S. J. Triezenberg, 1991, Gene, 103:235–238).

TABLE 14

Epitopes within $U_L48$ (VP16) of HSV-2 recognized by lesion- and PBMC-derived CD4 TCC. Data are delta cpm [³H] thymidine incorporation compared to media, which was less than 500 cpm in each case.

| TCC | | whole virus antigen | | recombinant HSV-2 protein[1] | | HSV-2 VP16 peptide | |
|---|---|---|---|---|---|---|---|
| Name | origin | HSV-1 | HSV-2 | VP16 1–492 | β-gal-VP16 180–492 | amino acids | delta cpm |
| newly reported epitopes | | | | | | | |
| RH.13 | lesion | 3,340 | 3,407 | 32,991 | nd | 185–197 | 55,614 |
| KM.7 | lesion | 6,093 | 5,847 | 5,627 | nd | 209–221 | 10,075 |
| BM.17 | PBMC | 30,784 | 13,777 | nd | 45,958 | 437–449 | 79,723 |
| SB.17 | PBMC | 2,207 | 4,187 | nd | 12,178 | 437–449 | 36,442 |
| previously reported epitopes | | | | | | | |
| ESL4.34 | lesion | 256 | 8,780 | 17,302 | nd | 389–401 | 12,968 |
| | | | | | | 393–405 | 95,942 |
| ESL3.334 | lesion | 253 | 14,232 | 22,754 | 16,434 | 430–444 | 27,283 |
| 1A.B.25 | lesion | 414 | 33.493 | 24,919 | 41,123 | 431–440 | 38,664 |

[1]VP16 1–492 (baculovirus-derived) was used at 1 μg/ml. β-gal-VP16 180–492 was used at 1:1,000 dilution.
[2]Peptides were used at 1 μM.
na = not available
nd = not done

TABLE 15

Cytolytic activity of lesion-derived, tegument-specific CD4 TCC with summary of fine specificity and HLA restriction. Results are percent specific release at an effector to target ratio of 20:1 except ESL4.34 (10:1). Auto = autologous EBV-LCL as target cells; allo = allogeneic EBV-LCL mismatched at the relevant HLA locus (if known) or mismatch at HLA DR and DQ.

| | | | cytolysis assay target | | | | | |
|---|---|---|---|---|---|---|---|---|
| TCC | specificity[1] | HLA restriction[2] | auto HSV-2 | auto peptide | auto mock | allo HSV-2 | allo peptide | allo mock |
| newly reported epitopes | | | | | | | | |
| RH.13 | VP16 185–197 | DR[4] | 62.5 | 55.2 | −0.9 | 9.6 | 0.3 | 1.8 |
| KM.7 | VP16 209–221 | DR[4] | 38.7 | 43.6 | 2.7 | −2.2 | 4.3 | −1.1 |
| BM.17 | VP16 437–449 | DQB1*0501 | 10.1 | 28.5 | −0.3 | nd | nd | nd |
| SB.17 | VP16 437–449 | DQB1*0501 | 48.7 | 60.6 | 5.4 | nd | nd | nd |
| previously described epitopes | | | | | | | | |
| ESL4.34 | VP16 393–405 | DRB1*0402 | 2.1 | 10.4 | 1.0 | 0.5 | 0.6 | 0.3 |
| ESL3.334 | VP16 430–444 | DQB1*0302 | 12.3 | 33.6 | 0.7 | 1.4 | 0.3 | 2.2 |
| 1A.B.25 | VP16 431–440 | DQB1*0201 | 24.3 | 42.2 | 1.9 | 1.7 | 2.1 | −0.4 | na = not available since epitope mapping was not done and synthetic antigenic peptide was not made.
nd = not done.
[1]Indicates peptide used (1 μM) to load targets in CTL assay for selected TCC.
[2]Maximum extent of definition of HLA restricting locus and/or allele. Subjects RH and KM were typed serologically; others were typed at the DNA level.

The HLA restriction of TCC BM.17 was studied in detail. Proliferation of TCC BM.17 and the similar clone SB.17 was inhibited 90% by anti-DQ, but less than 25% by anti-DR or anti-DP mAb. Donors BM and SB are heterozygous for HLA DQB1*0201/0501. At high concentrations of peptide, both DQB1*0201- and DQB1*0501 homozygous EBV-LCL appeared to present antigen to TCC BM.17. However, DQB1*0501 homozygous cells presented peptide much more efficiently than DQB1*0201 homozygous cells (FIG. 19). Thus, three different but overlapping epitopes in VP16 431–449 are presented by HLA DQB1*0302, DQB1*0201, and DQB1*0501.

CTL Activity of Tegument-Specific CD4 T-Cell Clones

Cytotoxic activities of the CD4 TCC with newly and previously identified specificities were tested using EBV-LCL target cells. All clones tested displayed cytolytic activity towards peptide-loaded target cells. Cytolytic activity against target cells infected with HSV-2 showed some variability. Among the seven VP16-specific T-cell clones tested, six displayed greater than 10% cytotoxicity towards HSV-2-infected target cells.

An additional epitope, included in amino acids 288–307 of $U_L48$ (VP16) (RELNHIREHLNLPLVRSA; SEQ ID NO: 32), was demonstrated to have reactivity with a CD4+ T cell clone. This epitope is recognized in association with the HLA class II molecule DRB1*1501, which is fairly prevalent in most human populations.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A pharmaceutical composition comprising a herpes simplex virus (HSV) polypeptide,
wherein the polypeptide is up to 15 amino acids in length and comprises amino acids 14–22, 21–35, 45–59, 49–57, or 49–63 $U_L49$ (SEQ ID NO: 3),
and a pharmaceutically acceptable carrier.

2. The pharmaceutical composition of claim 1, wherein the polypeptide consists of amino acids 14–22, 21–35, 45–59, 49–57, or 49–63 $U_L49$ (SEQ ID NO: 3).

3. The pharmaceutical composition of claim 1, wherein the polypeptide is a fusion protein.

4. The pharmaceutical composition of claim 3, wherein the fusion protein is soluble.

5. The pharmaceutical composition of claim 1, further comprising an adjuvant.

6. A pharmaceutical composition comprising an isolated polynucleotide that encodes an HSV polypeptide that is up to 15 amino acids in length and comprises an amino acid sequence consisting of amino acids 14–22, 21–35, 45–59, 49–57, or 49–63 of $U_L49$ (SEQ ID NO: 3).

7. The pharmaceutical composition of claim 6, wherein the polypeptide consists of amino acids 14–22, 21–35, 45–59, 49–57, or 49–63 $U_L49$ (SEQ ID NO: 3).

8. The pharmaceutical composition of claim 7, further comprising an adjuvant.

9. A method of inducing an immune response to an HSV infection in a subject comprising administering the composition of claim 1 to the subject.

10. A method of inducing an immune response to an HSV infection in a subject comprising administering the composition of claim 7 to the subject.

11. A method of treating an HSV infection in a subject comprising administering the composition of claim 1 to the subject.

12. A method of treating an HSV infection in a subject comprising administering the composition of claim 7 to the subject.

* * * * *

UNITED STATES PATENT AND TRADEMARK OFFICE
CERTIFICATE OF CORRECTION

| | | |
|---|---|---|
| PATENT NO. | : 7,037,509 B2 | |
| APPLICATION NO. | : 10/882074 | |
| DATED | : May 2, 2006 | |
| INVENTOR(S) | : David M. Koelle et al. | |

It is certified that error appears in the above-identified patent and that said Letters Patent is hereby corrected as shown below:

Please add to Column 1 in a separate paragraph below the second paragraph, the following statement:

--This invention was made with government support under grant Number AI34616 and grant Number AI30731 awarded by the National Institutes of Health. The government has certain rights in the invention.--

Signed and Sealed this

Nineteenth Day of September, 2006

JON W. DUDAS
*Director of the United States Patent and Trademark Office*